US010882849B2

(12) United States Patent
Boi et al.

(10) Patent No.: US 10,882,849 B2
(45) Date of Patent: Jan. 5, 2021

(54) DIMERIC CONTRAST AGENTS

(71) Applicant: BRACCO IMAGING S.P.A., Milan (IT)

(72) Inventors: Valeria Boi, Strambino (IT); Roberta Napolitano, Aibiano d'Ivrea (IT); Luciano Lattuada, Cassina de'Pecchi (IT)

(73) Assignee: BRACCO IMAGING S.P.A., Milan (IT)

( * ) Notice: Subject to any disclaimer, the term of this patent is extended or adjusted under 35 U.S.C. 154(b) by 119 days.

(21) Appl. No.: 16/522,076

(22) Filed: Jul. 25, 2019

(65) Prior Publication Data

US 2019/0345142 A1 Nov. 14, 2019
US 2020/0331893 A9 Oct. 22, 2020

Related U.S. Application Data

(63) Continuation of application No. 16/060,754, filed as application No. PCT/EP2016/080621 on Dec. 12, 2016, now Pat. No. 10,407,412.

(30) Foreign Application Priority Data

Dec. 10, 2015 (EP) .................................. 15199220

(51) Int. Cl.
*A61B 5/055* (2006.01)
*C07D 403/12* (2006.01)
*C07D 257/02* (2006.01)
*A61K 49/12* (2006.01)
*A61K 49/10* (2006.01)

(52) U.S. Cl.
CPC .......... *C07D 403/12* (2013.01); *A61K 49/122* (2013.01); *C07D 257/02* (2013.01); *A61K 49/108* (2013.01)

(58) Field of Classification Search
None
See application file for complete search history.

(56) References Cited

U.S. PATENT DOCUMENTS

| 4,647,447 | A | 3/1987 | Gries et al. |
| 4,885,363 | A | 12/1989 | Tweedle et al. |
| 4,916,246 | A | 4/1990 | Felder et al. |
| 5,132,409 | A | 7/1992 | Felder et al. |
| 5,277,895 | A | 1/1994 | Platzek et al. |
| 5,876,698 | A | 3/1999 | Schmitt-Willich et al. |
| 5,980,864 | A | 11/1999 | Platzek et al. |
| 6,149,890 | A | 11/2000 | Uggeri et al. |
| 6,852,854 | B1 * | 2/2005 | Kovacs ................ C07C 229/16 534/10 |
| 7,208,140 | B2 | 4/2007 | Schirmer et al. |
| 10,407,412 | B2 * | 9/2019 | Boi ...................... C07D 257/02 |
| 2011/0177002 | A1 | 7/2011 | Zitzmann-Kolbe et al. |
| 2013/0296539 | A1 | 11/2013 | Bhushan |
| 2014/0086846 | A1 | 3/2014 | Grimmond et al. |
| 2015/0065711 | A1 | 3/2015 | Davis |

FOREIGN PATENT DOCUMENTS

| CN | 102727911 | | 7/2013 |
| DE | 19849465 | A1 | 4/2000 |
| DE | 10117242 | C1 | 5/2002 |
| EP | 0230893 | A2 | 8/1987 |
| EP | 0512661 | A1 | 11/1992 |
| EP | 0872479 | A1 | 10/1998 |
| WO | 9848844 | A2 | 11/1998 |
| WO | 9856775 | A1 | 12/1998 |
| WO | 2008126034 | A2 | 10/2008 |

OTHER PUBLICATIONS

Bechara, G. et al. "Polyazamacrocycles based on a tetraaminoacetate moiety and a (poly)pyridine intracyclic unit: direct synthesis and application to the photosensitization of Eu(III) and Tb(III) ions in aqueous solutions," Tetrahedron 2010 66:8594-8604.
Bordunov et al., "Synthesis of New Pyridinoazacrown Ethers Containing Aromatic and Heteroaromatic Proton Ionizable Substituents" J. Org. Chem. 1995, 60, 6097-6102.
Caravan et al., "Gadolinium (III) Chelates as MRI Contrast Agents: Structure, Dynamics, and Applications," Chem. Rev. 1999, 99, 2293-2352.
Douglass, et al., "Intramolecular Hydrophosphination/Cyclization of Phosphinoalkenes and Phosphinoalkynes Catalyzed by Organolanthanides: Scope, Selectivity, and Mechanism" J. Am. Chem. Soc. 2001, 123, 10221-10238.
Formanovsky, et al., "One Stage Monosubstitution in Cyclen-Two Novel Examples" Synthetic Communications, 1996 26(8), 1595-1603.
Fulton D. et al, "Efficient relaxivity enhancement in dendritic gadolinium complexes: effective motional coupling in medium molecular weight conjugates," Chem. Comm. 2005, 474-476.
Geant et al., "Highly Enantioselective Access to α-Dibenzylamino Ketones from Chiral Nonracemic α-Bromo α'-Sulfinyl Ketones by Dynamic Kinetic Resolution: Synthesis of (2R,1'S)-2[1-(Dibenzylamino)alkyl]oxiranes" Eur. J. Org. Chem. 2011, 1300-1309.
Glogard, et al., "Novel radical-responsive MRI contrast agent based on paramagnetic liposomes" Magnetic Resonance in Chemistry 2003, vol. 41, 585-588.
Greene et al. (Eds.), Protective Groups in Organic Synthesis, John Wiley & Sons, Inc., Chapter 5, pp. 152-179 (1981).
Greene et al. (Eds.), Protective Groups in Organic Synthesis, Third Edition, John Wiley & Sons, Inc., Chapter 7, pp. 494-653 (1999).
Hovland et al., "Gadolinium DO3A derivatives mimicking phospholipids; preparation and in vitro evaluation as pH responsive MRI contrast agents" J. Chem. Soc. Perkin Trans. 2, 2001; 929-933.

(Continued)

*Primary Examiner* — Michael G. Hartley
*Assistant Examiner* — Melissa J Perreira
(74) *Attorney, Agent, or Firm* — Vivicar Law, PLLC

(57) ABSTRACT

The present invention relates to new class of dimeric macrocycles capable of chelating paramagnetic metal ions, their chelated complexes with metal ions and the use thereof as contrast agents, particularly suitable for Magnetic Resonance Imaging (MRI) analysis.

8 Claims, No Drawings

(56) References Cited

OTHER PUBLICATIONS

Maeda et al., "Intramolecular Cyclization of N,N-di(oligooxyethylene)amines: A New Synthesis of Monoaza Crown Ethers" Tetrahedron 1982, vol. 38, No. 22, 3359-3362.
Manning et al., "Expeditious synthesis of 'P'-protected macrocycles en route to lanthanide chelate metal complexes" Tetrahedron Letters 46, (2005) 4707-4710.
Moore, "Selective Trialkylation of Cyclen with tert-Butyl Bromoacetate [1,4,7,10-Tetraazacyclododecane-1,4,7-triacetic acid, Tri-tert-butyl Ester Hydrobromide]" Org. Synth. 2008, 85,10-14.
PCT Search Report and Written Opinion for PCT/EP2016/080592, dated Jan. 23, 2017.
PCT Search Report and Written Opinion for PCT/EP2016/080621, dated Feb. 7, 2017.
Pinsker et al., "A Highly Efficient Type I β-Turn Mimetic Simulating an Asx-Pro-Turn-Like Structure." Organic Letters 2011; vol. 13, No. 13: 3502-3505.
Placidi, et al., "Aryl-phosphonate lanthanide complexes and their fluorinated derivatives: investigation of their unusual relaxometric behavior and potential application as dual frequency 1H/19F MRI probes" Chem. Eur. J. 2013, 19, 11644-11660.
PubMed Entry, 6-bromohexane-1,2,3,4,5-pentol (Dec. 12, 2007).
Tei, et al., "Thermodynamic stability, kinetic inertness, and relaxometric properties of monoamide derivatives of lanthanide(III) DOTA complexes" Dalton Transactions, 2015 vol. 44, 5467-5478.
Wyatt, et al., "An enantioselective synthesis of (R)-2-amino-1-hydroxyethylphosphonic acid by hydrolytic kinetic resolution of (±)-diethyl oxiranephosphonate" Tetrahedron Letters 40 (1999) 6481-6483.
Yuan et al., "Studies on Organophosphorus Compounds 91: A Novel Synthesis of 1-Hydrazinoalkylphosphonic Acids and Derivatives Thereof" 1996, 507-510.

* cited by examiner

DIMERIC CONTRAST AGENTS

CROSS-REFERENCE TO RELATED APPLICATIONS

This application is a continuation of U.S. application Ser. No. 16/060,754, filed Jun. 8, 2018, which is the national stage application of corresponding international application number PCT/EP2016/080621, filed Dec. 12, 2016, which claims priority to and the benefit of European application no. 15199220.3, filed Dec. 10, 2015, all of which are hereby incorporated by reference in their entirety.

FIELD OF THE INVENTION

The present invention relates to the field of diagnostic imaging and to novel contrast agents possessing improved relaxivity. More in particular, it relates to dimeric macrocycles capable of chelating paramagnetic metal ions, their chelated complexes with metal ions and the use thereof as contrast agents in Magnetic Resonance Imaging (MRI).

STATE OF THE ART

Magnetic Resonance Imaging (MRI) is a renowned diagnostic imaging technique increasingly used in clinical diagnostics for growing number of indications.

The undisputed success of this technique is determined by the advantages it offers, including a superb temporal and spatial resolution, the outstanding capacity of differentiating soft tissues and its safety, due to its non-invasiveness and the absence of any ionizing radiation, in contrast to, for instance, X-ray, PET and SPECT.

In MRI imaging the contrast is basically due to differences existing in the longitudinal T1 and the transverse T2 relaxation times of the water protons in the different body organs and tissues, which allows the in-vivo acquisition of high-resolution, three-dimensional images of the distribution of water.

The intensity of the signal recorded in MRI imaging stems, essentially, from the local value of the longitudinal relaxation rate 1/T1, and the transverse rate, 1/T2 of water protons, and increases with increasing of the 1/T1 value (of the longitudinal relaxation rate of water protons) while decreases with the increase of 1/T2. In other words, the shorter is T1, the higher is the intensity of the recorded signal in MRI, the better is the diagnostic image.

The strong expansion of medical MRI has further benefited from the development of a class of compounds, the MRI contrast agents, that act by causing a dramatic variation of nearby water proton relaxation rates in the tissues/organs/fluids wherein they distributes, thus adding relevant physiological information to the impressive anatomical resolution commonly obtained in the uncontrasted MRI images.

Contrast agents used in the MRI imaging technique typically include a paramagnetic metal ion which is complexed with a cyclic or acyclic chelating ligand, more typically a polyaminopolycarboxylic chelator. The most important class of MRI contrast agents is represented by the Gd(III) chelates which are currently used in about ⅓ of the clinical tests. Indeed, Gd(III) is highly paramagnetic with seven unpaired electrons and a long electronic relaxation time, making it an excellent candidate as a relaxation agent. On the other hand, the free metal ion $[Gd(H_2O)_8]^{3+}$ is extremely toxic for living organism even at low doses (10-20 micromol/Kg). Thus, in order to be considered as a potentially valuable MRI contrast agent, a Gd(III) complex shall display a high thermodynamic (and possibly kinetic) stability in order to prevent the release of toxic metal ion.

Preferred MRI contrast agent should furthermore display optimal relaxivity. Relaxivity ($r_{1p}$, $r_{2p}$), expressed in $mM^{-1} s^{-1}$ and usually measured at 298K and 20 MHz (approx. 0.5 T), is the intrinsic property of a paramagnetic complex which characterizes its capability to increase the nuclear magnetic relaxation rate, longitudinal ($1/T_1$) and transverse ($1/T_2$) respectively, of vicinal water protons and, thus, its efficacy as MRI contrast enhancing agent. In general terms, the higher the relaxivity of an MRI contrast agent, the greater its contrast enhancing capability and the stronger the contrast provided in recorded MRI images.

A number of complexes of paramagnetic metal ions are known in the art (see for instance: Caravan P. et al. Chem. Rev. 1999, 99, 2293-2352 and U.S. Pat. Nos. 4,647,447, 4,885,363; 4,916,246; 5,132,409; 6,149,890; and 5,980,864).

Dimeric complexes are disclosed for instance in U.S. Pat. No. 5,277,895, DE10117242, and DE19849465.

Examples of commercially available MRI contrast agents include the complex compound of the $Gd^{3+}$ ion with the DTPA ligand, marketed as MAGNEVIST®; the $Gd^{3+}$ complex of the DTPA-BMA ligand, marketed as OMNISCAN®; the $Gd^{3+}$ complex of BOPTA, known as gadobenate Dimeglumine and marketed as MultiHance™; the $Gd^{3+}$ complex of the DOTA ligand, marketed as DOTAREM®; the $Gd^{3+}$ complex of the hydroxylated tetraaza macrocyclic ligand known as HPDO3A, long time marketed as ProHance® and that of the corresponding butyl-triol derivative, known as Gadobutrol and marketed ad Gadavist®. All the above contrast agents comprise a single chelating unit, and are Non-Specific Agents (NSA), designed for a general use.

While known compounds generally provide a quality of the imaging capable of meeting and satisfying the present needs of radiologists resulting in accurate and detailed diagnostic information, there is nevertheless still the need for new compounds with improved contrast imaging features, such as increased relaxivity.

In particular, compounds with improved relaxivity could reduce the required dose of the paramagnetic contrast agent and possibly shorten the acquisition time of the imaging process.

SUMMARY OF THE INVENTION

The present invention generally relates to novel macrocyclic chelating ligands useful for the preparation of paramagnetic complexes having particularly favorable characteristics, among others in terms of improved relaxivity.

In general terms, an aspect of the present invention relates to novel dimeric ligands comprising two tetraaza macrocycles with a hydroxylated residue on a nitrogen atom of the chelating cage linked to one another through amine group(s).

The invention further relates to respective chelated complexes of said chelating ligands with a paramagnetic metal ion and, especially, with $Gd^{3+}$, or of a physiologically acceptable salt thereof.

A further aspect of the invention relates to the use of such chelated complexes as contrast agents, in particular for the diagnostic imaging of a human or animal body organ or tissue by use of the MRI technique.

In a further aspect the invention relates to a manufacturing process for the preparation of the provided ligands, their complex compounds with a paramagnetic metal ion, and the pharmaceutical acceptable salt thereof and their use in the preparation of a diagnostic agent.

According to another aspect, the invention relates to a pharmaceutically acceptable composition comprising at least one paramagnetic complex compound of the invention, or a pharmaceutical salt thereof, in admixture with one or more physiologically acceptable carriers or excipients. Said compositions are useful in particular as MRI contrast media, to provide diagnostically useful images of human or animal body organs or tissues.

Therefore, in another aspect, the present invention refers to a method for the diagnostic imaging of a body organ, tissue or region by use of MRI technique that comprises the use of an effective dose of a compound of the invention.

DETAILED DESCRIPTION OF THE INVENTION

An object of the present invention are chelating ligands of formula (I)

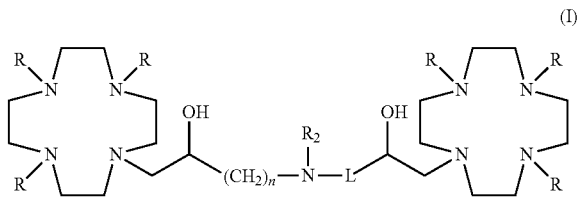

where:
R is —CH($R_1$)—COOH, where:
  $R_1$ is H or a $C_1$-$C_3$ alkyl chain that is optionally substituted by a $C_1$-$C_3$ alkoxy or $C_1$-$C_3$ hydroxyalkoxy group;
n is 1 or 2;
$R_2$ is selected from the group consisting of: an aryl ring; a cycloalkyl ring; a $C_1$-$C_5$ alkyl substituted by one ore more $C_1$-$C_8$ hydroxyalkoxy groups, or by a cycloalkyl ring; a group of formula —(CH$_2$)$_s$CH($R_3$)-G; and a $C_5$-$C_{12}$ hydroxyalkyl comprising at least 2 hydroxyl groups;
in which
  s is 0, 1 or 2;
  G is a group selected from —PO(O$R_4$)$_2$, —PO($R_5$)(O$R_4$) and —COOH;
  $R_3$ is H, or an arylalkylene or cycloalkyl-alkylene having from 1 up to 3 carbon atoms in the alkylene chain;
  $R_4$ independently of one another is H or $C_1$-$C_5$ alkyl;
  $R_5$ is an aryl or cycloalkyl ring, or $C_1$-$C_5$ alkyl which is optionally substituted by an aryl or cycloalkyl ring; and
L is a $C_1$-$C_6$ alkylene, optionally interrupted by one or more —N(R'$_2$)— groups, and optionally substituted by one or more substituent groups selected from hydroxyl, $C_1$-$C_3$ alkoxy and $C_1$-$C_3$ hydroxyalkoxy, where
R'$_2$ is, independently, as defined for $R_2$.
Preferably in the above compounds of formula (I) $R_1$ is H.
In the present description, and unless otherwise provided, the expression "alkyl" comprises within its meaning any linear or branched hydrocarbon chain, preferably comprising up to 12 carbon atoms. In particular "$C_1$-$C_{12}$ alkyl" comprises within its meaning a linear or branched chain comprising from 1 to 12 carbon atoms such as: methyl, ethyl, propyl, iso-propyl, butyl, iso-butyl, tert-butyl, pentyl, iso-pentyl, tert-pentyl, hexyl, iso-hexyl, heptyl, iso-heptyl, octyl, and the like. Similarly, the term "$C_1$-$C_3$ alkyl" comprises within its meaning a linear or branched chain comprising from 1 to 3 carbon atoms such as, for instance, methyl, ethyl, propyl and iso-propyl; the term "$C_1$-$C_6$ alkyl" comprises within its meaning a linear or branched chain comprising from 1 to 6 carbon atoms such as: methyl, ethyl, propyl, iso-propyl, butyl, iso-butyl, tert-butyl, pentyl, hexyl and the like; and the term "$C_5$-$C_7$ alkyl" comprises within its meaning any linear or branched chain comprising from 5 to 7 carbon atoms such as pentyl, iso-pentyl, tert-pentyl, hexyl, iso-hexyl, tert-hexyl, heptyl, iso-heptyl and tert-heptyl.

By analogy, the expression "alkylene" comprises within its meaning a bivalent linear or branched chain derived by any of the above hydrocarbon chains by removal of two hydrogen atoms from different carbon atoms, e.g. including $C_1$-$C_6$ alkylene such as for instance a methylene, ethylene, (iso)propylene and so on.

The term "hydroxyalkyl" comprises within its meaning any of the corresponding alkyl chain wherein one or more hydrogen atoms are replaced by hydroxyl groups. Suitable examples include $C_1$-$C_3$ hydroxyalkyl such as hydroxymethyl (—CH$_2$OH), hydroxyethyl (—CH$_2$CH$_2$OH), hydroxypropyl (—CH$_2$CH$_2$CH$_2$OH), dihydroxypropyl, (—CH$_2$CH$_2$OHCH$_2$OH and —CH(CH$_2$OH)$_2$) and the like, and polyhydroxyalkyls or "polyols", as used herein interchangeably, in which at least two and, preferably, three or more hydrogen atoms of the hydrocarbon chain are replaced by hydroxyl groups.

For instance, and unless otherwise provided, the expression "$C_5$-$C_{12}$ polyol" (or "$C_5$-$C_{12}$ polyhydroxyalkyl") comprises within its meaning any of the corresponding $C_5$-$C_{12}$ alkyl moiety in which 2 or more, e.g. from 2 to 11 hydrogen atoms have been replaced by hydroxyl groups. Among them, $C_5$-$C_{10}$ polyols are preferred, and $C_5$-$C_7$ polyols are particularly preferred. Examples of $C_5$-$C_7$ polyols include pentylpolyols (or polyhydroxypentyls) such as pentyl-diols, pentyl-triols, pentyl-tetraols and pentyl-pentaol, respectively comprising from 2, 3, 4 and 5 hydroxyl groups on a $C_5$ alkyl chain; hexyl-polyols (or polyhydroxyhexyls) analogously comprising from 2 to 6 hydroxyl groups on a $C_6$ alkyl chain; and heptyl-polyols (or polyhydroxyheptyls) comprising from 2 to 7 hydroxyl groups on a $C_7$ alkyl chain.

The term "alkoxy" comprises within its meaning an alkyl chain as above defined further comprising one or more oxygen atoms; examples include, for instance, alkyl-oxy (or —Oalkyl) groups such as methoxy, ethoxy, n-propoxy, iso-propoxy and the like, and alkyl-(poly)oxy in which the alkyl chain is interrupted by one or more, e.g. up to three, oxygen atoms.

The term "hydroxyalkoxy" comprises within its meaning any of the above alkyloxy residues further comprising one or more hydroxyl (—OH) in the alkyl chain such as, for example, —OCH$_2$OH, —OCH$_2$CH$_2$OH, —OCH$_2$CH$_2$CH$_2$OH, —OCH$_2$OCH$_2$OH, —OCH$_2$CH$_2$OCH$_2$CH$_2$OH, —OCH$_2$CH(OH)CH$_2$—OCH$_2$CH$_2$OH, and the like.

The term "hydroxyalkoxyalkylene" (or "hydroxyalkoxyalkylene") comprises within its meaning any of the above hydroxyalkoxy where the linking group of the residue is an alkylene chain —(CH$_2$)$_r$—, including $C_2$-$C_{10}$ hydroxyalkoxy-alkylenes e.g. of formula —(CH$_2$)$_r$—[(O—(CH$_2$)$_r$]$_r$(CH$_2$)$_s$OH, where each r is independently 1 or 2, and s is 0, 1 or 2.

The expression "carboxyl" comprises within its meaning a residue of formula —COOH, or comprising said —COOH residue, such as the groups of formula —(CH$_2$)$_s$—COOH or —[O(CH$_2$)$_n$]$_s$—COOH, where s and n are as above defined.

The term "aryl" or "aryl ring" refers to an aromatic hydrocarbon and, preferably, a phenyl ring. Unless otherwise specifically provided, aryls according to the invention can be either unsubstituted or substituted with one or more, equal or different, substituent groups, for instance selected from hydroxyl (OH), halogen, C$_1$-C$_3$ alkyl, C$_1$-C$_3$ alkoxy, C$_1$-C$_3$ hydroxyalkyl, carboxy, carbamoyl, nitro, —NH$_2$, or C$_1$-C$_3$ alkyl- or dialkylamino, preferably from hydroxyl, halogen, C$_1$-C$_3$ alkyl or alkoxy, or carboxy and, more preferably, from C$_1$-C$_3$ alkyl or alkoxy, —CH$_2$COOH, and —COOH.

The term "cycloalkyl ring" (or "cycloalkyl") as used herein comprises within its meaning a saturated (i.e. cycloaliphatic), either carbocyclic or heterocyclic ring.

Suitable examples include a C$_5$-C$_7$ carbocyclic ring e.g. a cyclohexyl ring. Unless otherwise specifically provided, carbocyclic rings according to the invention can be either unsubstituted or substituted with one or more, equal or different, substituent groups for instance selected from hydroxyl halogen, C$_1$-C$_3$ alkyl, C$_1$-C$_3$ alkoxy, C$_1$-C$_3$ hydroxyalkyl, carboxyl, carbamoyl, nitro, —NH$_2$, or C$_1$-C$_3$ alkyl- or dialkylamino, preferably from hydroxyl, halogen, C$_1$-C$_3$ alkyl or alkoxy or carboxy and, more preferably, from C$_1$-C$_3$ alkyl or alkoxy, —CH$_2$COOH, and —COOH.

"Cycloalkyl ring" according to the invention further include a saturated heterocyclic ring (or heterocycle) e.g., preferably, a 5-6 membered saturated ring comprising a nitrogen atom in the cyclic chain and, optionally, another, equal or different, heteroatom selected from N, O and S. Suitable examples include heterocycles such as pyrrolidine, piperazine, morpholine and piperidine, wherein this last is particularly preferred. Nitrogen-containing heterocycles according to the invention preferably comprise one or more substituents groups linked to the carbon atom(s) of the cycle, e.g. selected from hydroxyl, C$_1$-C$_3$ hydroxyalkyl, C$_1$-C$_3$ alkoxy, C$_1$-C$_3$ hydroxyalkoxy, C$_1$-C$_3$ hydroxyalkoxy-alkyl, and a carboxyl such as —(CH$_2$)$_s$—COOH or —[O(CH$_2$)$_n$]$_s$—COOH, as above defined.

From all the above, having defined the meaning for alkyl, alkylene, aryl and cycloalkyl, any composite-name such as alkyl-aryl, aryl-alkylene, cycloalkyl-alkylene and the like should be clear to a skilled person.

For instance the term alkylaryl (or alkyl-aryl) comprises within its meaning an aryl group further substituted by an alkyl, (e.g. p-ethyl-phenyl; pC$_2$H$_5$—C$_6$H$_5$—) while the term arylalkylene (or aryl-alkylene) or cycloalkyl-alkylene comprises within its meaning an alkyl further substituted by an aryl (e.g. phenyl-ethylene=C$_6$H$_5$—C$_2$H$_4$—) or by a cycloalkyl (e.g. cyclohexyl-ethylene=C$_6$H$_{11}$—C$_2$H$_4$—); and the like.

In the present description the term "protecting group" designates a protective group adapted for preserving the function of the group to which it is bound. Specifically, protective groups are used to preserve amino, hydroxyl or carboxyl functions. Appropriate carboxyl protective groups may thus include, for example, benzyl, alkyl e.g. tert-butyl or benzyl esters, or other substituents commonly used for the protection of such functions, which are all well known to those skilled in the art [see, for a general reference, T. W. Green and P. G. M. Wuts; Protective Groups in Organic Synthesis, Wiley, N.Y. 1999, third edition].

Moreover, the terms "moiety" or "moieties", "residue" or "residues" are herewith intended to define the residual portion of a given molecule once properly attached or conjugated, either directly or through any suitable linker, to the rest of the molecule.

The compounds of the above formula (I) may have one or more asymmetric carbon atom, otherwise referred to as a chiral carbon atom, and may thus give rise to diastereomers and optical isomers. Unless otherwise provided, the present invention further includes all such possible diastereomers as well as their racemic mixtures, their substantially pure resolved enantiomers, all possible geometric isomers, and pharmaceutical acceptable salts thereof.

The present invention further relates to compounds of the above formula (I) in which each of the acidic groups, either including the carboxylic groups R linked to the nitrogen atoms of the macrocycles or any other optional acidic group, e.g. on R$_2$, may be in the form of a pharmaceutically acceptable salt, or of a derivative in which the acidic group is suitably protected with an appropriate protecting group (Pg) as above defined, e.g., preferably, of a C$_1$-C$_5$ alkyl ester and, more preferably, of a tert-butyl ester, finding for instance application as such, or as suitable precursor or intermediate compound in the preparation of a desided compound of formula (I) or of a suitable paramagnetic complex or salt thereof.

In one embodiment, the invention relates to dimeric compounds of formula (I) in which L is a C$_1$-C$_6$ alkylene chain.

Suitable examples include dimers of formula (II)

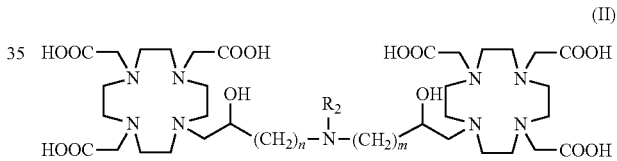

(II)

in which:

n is 1 or 2;

m is 1, 2, 3, 4, 5 or 6; and

R$_2$ is as defined for compounds of formula (I).

In one embodiment, in the above compounds of formula (II) R$_2$ is an aryl or a cycloalkyl ring, e.g., preferably, a phenyl or a cyclohexyl ring.

In another embodiment the invention relates to compounds of formula (II) in which R$_2$ is a C$_5$-C$_{12}$ hydroxyalkyl comprising at least two hydroxyl groups.

Suitable examples include compounds in which in the formula (II) R$_2$ is a C$_5$-C$_{12}$ polyhydroxyalkyl (or C$_5$-C$_{12}$ polyol) having from 2 to 11 and, preferably, from 3 to 10 hydroxyl groups on the C$_5$-C$_{12}$ alkyl chain.

Preferably, R$_2$ is the residue of a C$_5$-C$_7$ polyol e.g. selected from pentyl-polyols (or polyhydroxypentyls) comprising at least 2, and preferably from 2 to 4 hydroxyl groups on the C$_5$ alkyl chain; hexyl-polyols comprising at least 2, and preferably from 2 to 5 hydroxyl groups on the C$_6$ alkyl chain; and heptyl-polyols comprising at least 2 and, and preferably from 3 to 6 hydroxyl groups on the C$_7$ alkyl chain.

In particular, in one preferred embodiment the invention relates to compounds of formula (II A)

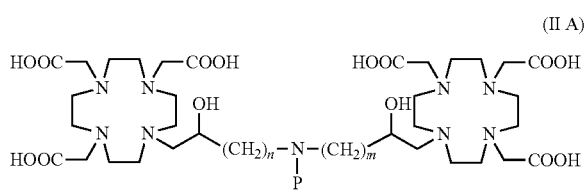

in which P is a $C_5$-$C_7$ polyol selected from a pentyl-tetraol of formula

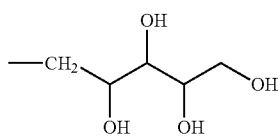

and a hexyl-pentaol of formula

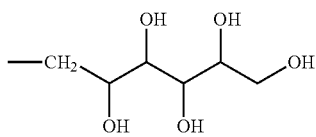

and n and m are as defined for compounds of formula (II).

Preferably, in the compounds of formula (II A) n and m, independently to one another, are 1 or 2. More preferably are both 1.

In a particularly preferred embodiment, the invention relates to a dimeric compound according to the above formula (II A), having the formula

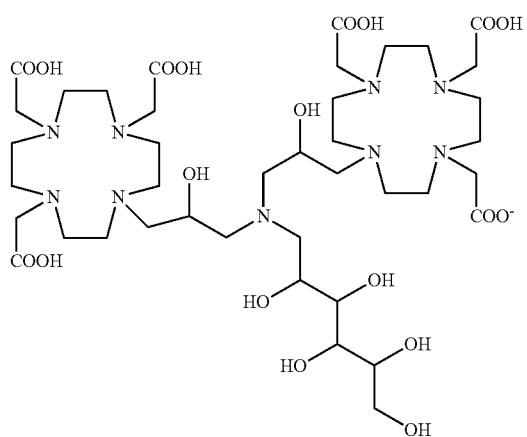

In a further embodiment, the invention relates to compounds according to the formula (II) in which $R_2$ is a group of formula —$(CH_2)_s CH(R_3)$-G where s, $R_3$ and G are as above defined for compounds of formula (I).

Preferably, in these compounds $R_3$ is H or an arylalkylene or cycloalkyl-alkylene selected from benzyl, phenyl-ethyl, cyclohexyl-methyl and cyclohexyl-ethyl; and G is a group of formula —$PO(OR_4)_2$, —$PO(R_5)(OR_4)$ and —COOH, in which $R_4$ is H or a tert-butyl, and $R_5$ is selected from an optionally substituted phenyl or cyclohexyl ring and a $C_1$-$C_5$alkyl chain, e.g., preferably, a methyl, ethyl or propyl group, which is substituted or not by an aryl or cycloalkyl ring such as a benzyl, phenyl-ethyl, cyclohexyl-methyl or cyclohexyl-ethyl group.

More preferably in the above compounds $R_3$ is H.

In particular, in one preferred embodiment the invention relates to compounds of formula (II B)

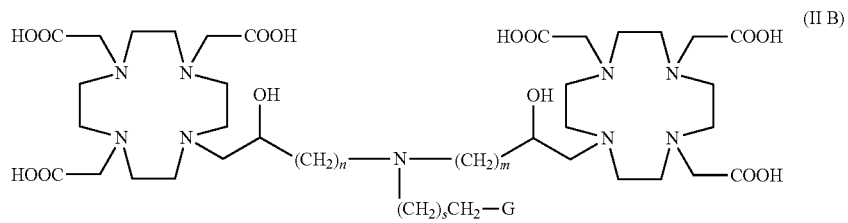

in which:

s is 0 or an integer from 1 to 2;

G is a group selected from —$PO(OR_4)_2$, —$PO(R_5)(OR_4)$ and —COOH, where $R_4$ is as is H or a tert-butyl and, preferably, is H; $R_5$ is an optionally substituted phenyl or cyclohexyl ring, or a $C_1$-$C_3$ alkyl substituted or not by an aryl or cycloalkyl ring such as benzyl, phenyl-ethyl, cyclohexyl-methyl or cyclohexyl-ethyl; and m and n are as said for the compounds of formula (II).

In a particularly preferred embodiment, the invention relates to compounds formula (II B) in which G is selected from —$PO(OH)_2$ and —COOH; s is 0 or 1; n and m, independently to one another, are 1 or 2 and, preferably, are both 1.

According to an additional embodiment, the invention relates to compounds of formula (II) in which $R_2$ is a $C_1$-$C_5$ alkyl which is substituted by one or two $C_1$-$C_8$ hydroxyalkoxy groups, or by a cycloalkyl ring.

In one preferred embodiment $R_2$ is a $C_1$-$C_5$ alkyl substituted by a $C_1$-$C_8$ hydroxyalkoxy group.

Suitable examples include dimers of formula (II) in which $R_2$ is a $C_2$-$C_{10}$ hydroxyalkoxy-alkylene e.g. selected from the groups of formula —$CH_2(OCH_2CH_2)_s OCH_2OH$, —$CH_2(CH_2OCH_2)_r CH_2OH$ and —$(CH_2)_r$—$O(CH_2)_r OH$, where r and s are as said.

Preferred among them are compounds of formula (II C)

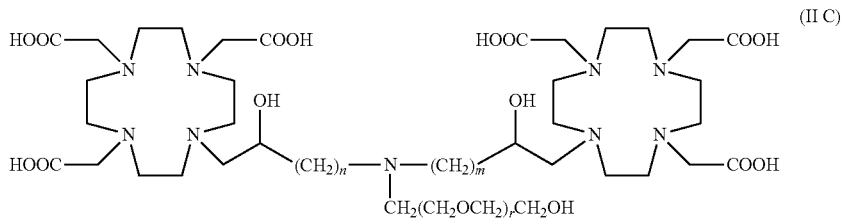

(II C)

in which each n, m and r, independently the one another, is an integer from 1 to 2.

Particularly preferred are compounds of formula (II C) in which n and m are both 1.

In another embodiment $R_2$ is a $C_1$-$C_5$ alkyl substituted by two $C_1$-$C_8$ hydroxyalkoxy groups.

Suitable examples include compounds of formula (II) in which $R_2$ is a branched $C_1$-$C_5$ alkyl, e.g. isopentyl or isobutyl, which is substituted by two $C_1$-$C_8$, and, preferably, $C_1$-$C_5$ hydroxyalkoxy groups.

Preferably, $R_2$ is a isopropylen or, more preferably, a isobutylen bearing two terminal polyhydroxyalkoxy groups selected from —OCH$_2$(CH$_2$OH)$_2$ and —OCH$_2$(CH$_2$CH$_2$OH)$_2$.

In a still further embodiment the invention relates to compounds of formula (II) in which $R_2$ is a $C_1$-$C_5$ alkyl substituted by a cycloalkyl ring.

Suitable examples include compounds in which $R_2$ is a $C_1$-$C_5$ alkyl substituted by a saturated $C_5$-$C_7$ carbocyclic ring such as a cyclohexyl ring, e.g., preferably, a cyclohexyl-alkylene having 1, 2 or 3 carbon atoms in the alkylene chain.

More preferably, $R_2$ is a $C_1$-$C_5$ alkyl substituted by a saturated $C_5$-$C_7$ heterocycle, e.g. a piperidine or a piperidine derivative having one or more e.g. from 1 to 8 substituents groups linked to the carbon atom(s) of the heterocycle.

In particular, in a further embodiment the invention relates to dimers of formula (II D)

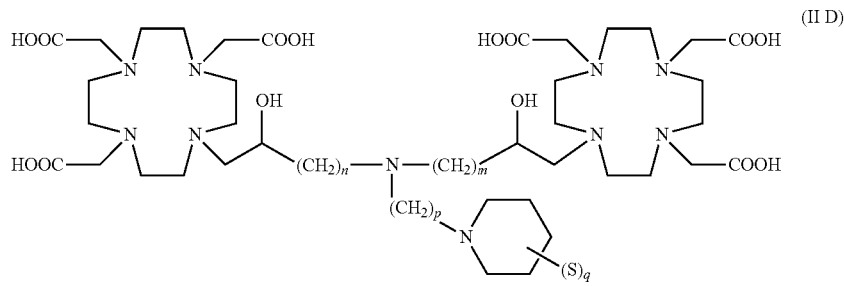

(II D)

in which
n and m are, each independently, 1 or 2 and, preferably, are both 1;
p is an integer from 1 to 3;
q is and integer from 1 to 8, and
S is a substituent group linked to a carbon atom of the piperidine ring, e.g. selected from the group consisting of: hydroxyl, $C_1$-$C_3$ hydroxyalkyl, $C_1$-$C_3$ alkoxy, $C_1$-$C_3$ hydroxyalkoxy, $C_1$-$C_3$ hydroxyalkoxy-alkylene, and carboxyl such as —(CH$_2$)$_s$—COOH and —OCH$_2$—COOH where s is as above said.

For instance, in one embodiment in the above compounds of formula (II D) q is 1, and S is a group selected from hydroxyl, $C_1$-$C_3$ hydroxyalkyl, $C_1$-$C_3$ hydroxyalkoxy and carboxyl such as —(CH$_2$)$_s$—COOH or —OCH$_2$—COOH and, more preferably, from hydroxyl, —CH$_2$OH, and —COOH that is linked to the $C_3$ carbon atom of the ring.

Preferably, in the above compounds formula (II D) q is an integer from 2 to 8, and the compounds comprise a piperidine ring having from 2 to 8, preferably from 2 to 6 and, more preferably, from 3 to 5 e.g. 3, 4, or 5 substituent groups S linked to one or more carbon atom(s) of the ring, that are each independently selected from hydroxyl, $C_1$-$C_3$ hydroxyalkyl, $C_1$-$C_3$ alkoxy, $C_1$-$C_3$ hydroxyalkoxy, $C_1$-$C_3$ hydroxyalkoxy-alkylene, and carboxyl such as —(CH$_2$)$_s$—COOH or —(OCH$_2$)$_s$—COOH.

According to an alternative embodiment, the invention relates to compounds according to the formula (I) in which L is a $C_1$-$C_6$ alkylene chain interrupted by one or two —N(R'$_2$)— groups.

Suitable examples include dimeric compounds of formula (III)

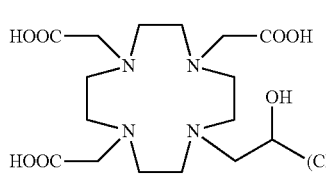 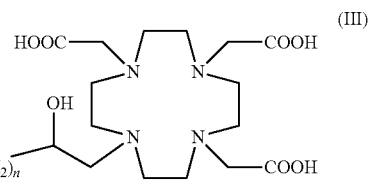

(III)

in which:
each n, r and d is, independently, 1 or 2; and
$R_2$ and $R'_2$ are as defined for the compounds of formula (I).

In one embodiment, in the above formula (III) d is 1, and the invention relates to dimers comprising two macrocyclic residues having a hydroxylated pendant arm bound to a nitrogen atom of the chelating cage linked to one another by means of a diamine group of formula —N($R_2$)—$(CH_2)_r$—N($R'_2$)—

In one embodiment, in the above compounds of formula (III) $R_2$ and $R_2'$, equal of different, are each independently selected from $R_2$ meanings.

Preferably, in the compounds of formula (III) $R_2'$ is the same as $R_2$.

In particular, in one preferred embodiment the invention relates to dimeric compounds of formula (IV)

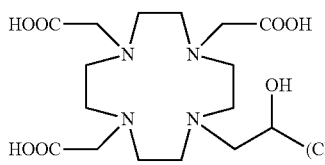 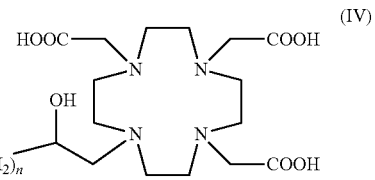

(IV)

in which each n and r is, independently, 1 or 2, and $R_2$ is as said for compounds of formula (II), including encompassed formulae from (II A) to (II D).

Suitable examples include compounds of formula (IV) in which $R_2$ is selected from the groups of formula —$CH_2$($OCH_2CH_2$)$_s$$OCH_2OH$, —$CH_2$($CH_2OCH_2$)$_r$$CH_2OH$ and —$(CH_2)_r$—O$(CH_2)_r$OH, in which r and s are as said. Preferably, $R_2$ is —$CH_2$($CH_2OCH_2$)$_r$$CH_2OH$, where r is 1 or 2.

According to a more preferred embodiment, in the above formula (IV) $R_2$ is a group of formula —$(CH_2)_s$CH($R_3$)-G where s, $R_3$ and G are as defined for compounds of formula (I).

Preferably, in these compounds $R_3$ is H or an arylalkylene or cycloalkyl-alkylene e.g. selected from benzyl, phenylethyl, cyclohexyl-methyl and cyclohexyl-ethyl; G is a group of formula —PO(O$R_4$)$_2$, —PO($R_5$)(O$R_4$) and —COOH in which $R_4$ is H or a tert-butyl and, preferably, is H, and $R_5$ is an optionally substituted phenyl or cyclohexyl ring, or a $C_1$-$C_3$ alkyl such as methyl, ethyl or propyl substituted or not by an aryl or cycloalkyl ring.

In particular, in one preferred embodiment the invention relates to dimers of formula (IV A)

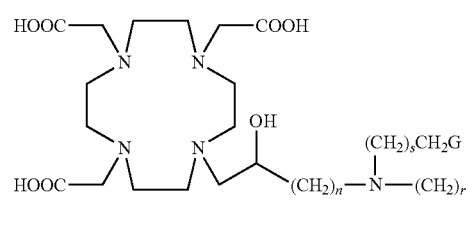 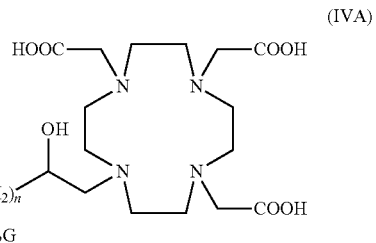

(IVA)

in which n is an integer from 1 to 2 and, preferably is 1;

r is 1 or 2;

s is 0 or an integer from 1 to 2, and preferably is 0 or 1; and

G a group selected from —PO(OR$_4$)$_2$ and —COOH where R$_4$ is H or a tert-butyl and, preferably, is H.

More preferably in the compounds of formula (IV A) n is 1, r is 2, and s is 0.

Particularly preferred according to the invention are dimers of formula (IV A) selected from

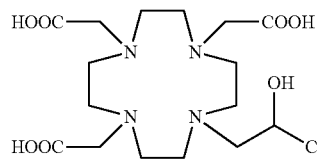

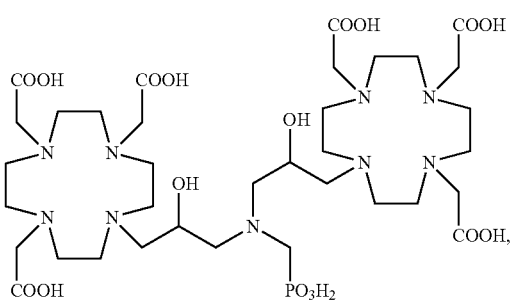

Compound 2 and

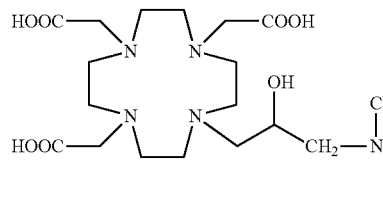

Particularly preferred compounds are those compounds of formula (I), or salts thereof, selected from the group consisting of:

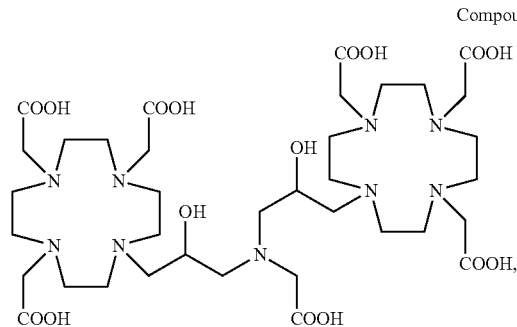

Compound 1

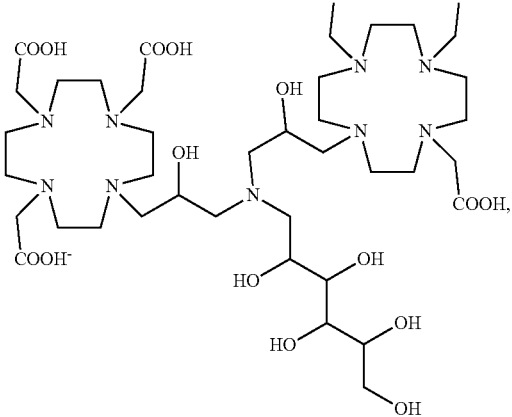

Compound 3

Compound 4

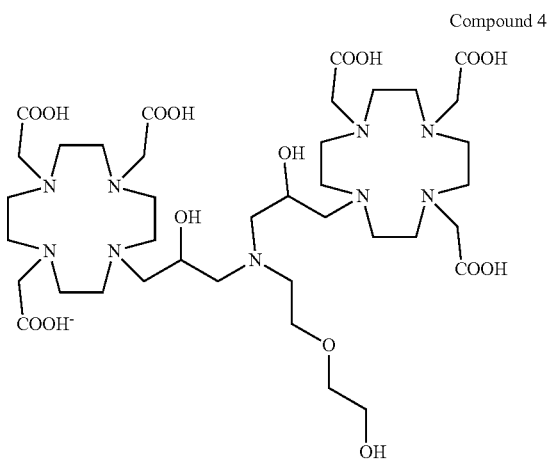

Compound 5

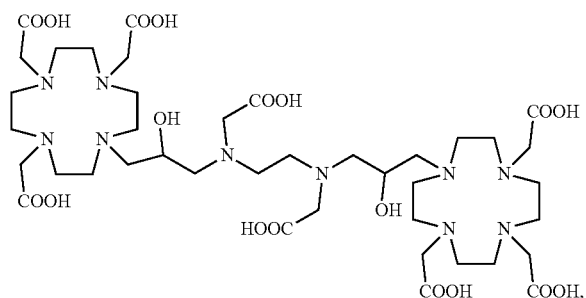

Compound 6

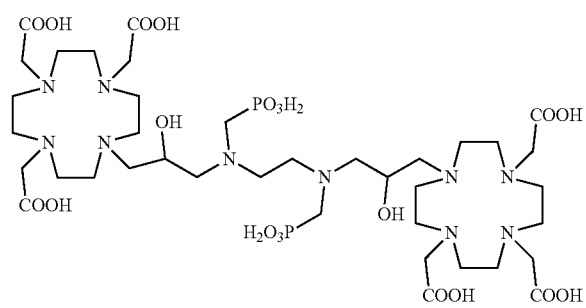

Compound 7

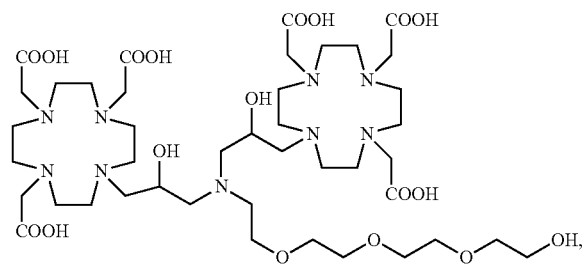

Compound 8

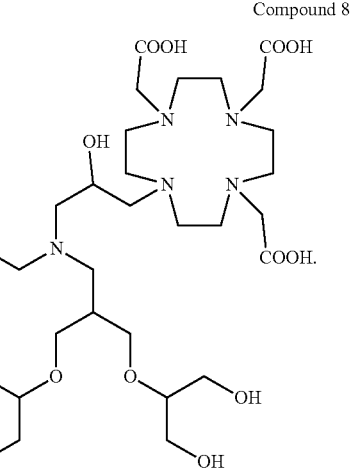

In a further aspect the invention relates to chelated complexes of the compounds of formula (I), hence encompassing those of formulae from (II) to (V), with two paramagnetic metal ions, or radionuclides, or of a suitable salt thereof.

Preferably, the paramagnetic metal ions are are equal to each other, and are selected in the group consisting of $Fe^{2+}$, $Fe^{3+}$, $Cu^{2+}$, $Cr^{3+}$, $Gd^{3+}$, $Eu^{3+}$, $Dy^{3+}$, $La^{3+}$, $Yb^{3+}$ or $Mn^{2+}$. More preferably, both the cheated paramagnetic metal ions are $Gd^{3+}$ ions.

Preferred radionuclides according to the invention providing complexes for use in radiotherapy or radiodiagnostics include $^{105}Rh$, $^{117m}Sn$, $^{99m}Tc$, $^{94m}Tc$, $^{203}Pb$, $^{67}Ga$, $^{68}Ga$, $^{44}Sc$, $^{72}As$, $^{110}In$, $^{111}In$, $^{113}In$, $^{90}Y$, $^{97}Ru$, $^{60}Cu$, $^{62}Cu$, $^{64}Cu$, $^{52}Fe$, $^{51}Mn$, $^{140}La$, $^{175}Yb$, $^{153}Sm$, $^{166}Ho$, $^{149}Pm$, $^{177}Lu$, $^{186/188}Re$, $^{165}Dy$, $^{166}Dy$, $^{142}Pr$, $^{159}Gd$, $^{211}Bi$, $^{212}Bi$, $^{213}Bi$, $^{214}Bi$, $^{149}Pm$, $^{67}Cu$, $^{198}Au$, $^{199}Au$, $^{161}Tb$, $^{167}Tm$, and $^{51}Cr$.

As formerly reported, both the compounds of formula (I) of the invention and the paramagnetic chelates thereof can also be in the form of a pharmaceutically acceptable salt, particularly as an addition salt with a physiologically compatible base or acid.

The term "pharmaceutically acceptable salt", as used herein, refers to derivatives of the compounds of the invention wherein the parent compound is suitably modified by converting any of the free acid or basic groups, if present, into the corresponding addition salt with any base or acid conventionally intended as being pharmaceutically acceptable.

Preferred cations of inorganic bases which can be suitably used to prepare a salt of the complexes or the ligands of the invention comprise, for instance, ions of alkali or alkaline-earth metals such as potassium, sodium, calcium or magnesium.

Preferred cations of organic bases comprise, for instance, those of primary, secondary and tertiary amines such as, for instance, ethanolamine, diethanolamine, morpholine, glucamine, N-methylglucamine, N,N-dimethylglucamine.

Preferred anions of inorganic acids which can be suitably used to prepare salts of the complexes of the invention comprise the ions of halo acids, for instance chlorides, bromides or iodides, as well as of other suitable ions such as sulfate.

Preferred anions of organic acids comprise those routinely used in pharmaceutical techniques for the salification preparation of salts of basic substances such as, for instance, acetate, succinate, citrate, fumarate, maleate or oxalate.

Preferred cations and anions of amino acids comprise, for instance, those of taurine, glycine, lysine, arginine, ornithine or of aspartic and glutamic acids.

The preparation of the compounds of formula (I), hence encompassing the compounds of formulae from (II) to (IV), and of the chelate complexes thereof, either as such or in the form of physiologically acceptable salts, represent a further object of the invention.

Compounds of formula (I), and the chelated complexes thereof, may be prepared through a general synthetic process comprising the following steps:

a) Obtaining a macrocyclic substrate 1 in a suitable protected form, e.g. in which the carboxylic groups of the substrate are protected as tert-butyl esters;
b) Obtaining a bridging molecule 2, in which any optional functional group(s) not involved with the coupling reaction with the substrate 1 is, optionally, suitably protected;
c) Coupling the bridging molecule 2 with two units of protected substrate 1, to give the desired compound of formula (I) in a suitably protected form or, alternatively, an intermediate thereof 3;
d) Optionally converting the obtained intermediate in the suitably protected compound of formula (I);
e) Removing any protecting group and isolating the chelating ligand of formula (I); and
f) Complexing the obtained ligand with a suitable paramagnetic metal ion and isolating the chelate complex, or the salt thereof.

To this extent, and unless otherwise indicated, the term "intermediate" (e.g. with reference to the compound 3 deriving from the reaction of the macrocyclic substrate 1 with an bridging molecule 2) refers to a molecule that requires one (or more) further reactions, e.g. deprotection/alkylation reaction(s) converting any optional protected nitrogen atom(s) of the bridging molecule 2 in the corresponding alkylated derivative(s), to give the desired product, i.e. in the specific case of the above general scheme, in a suitably protected dimeric compound of formula (I) according to step d). The single steps of the above general process, comprehensive of any variant thereof, particularly when referring to the steps of protection/deprotection and activation of known functional groups, may be carried out according to conventional methods known in the art.

For instance, suitable substrates 1A according to the step a) of the process of the invention, of formula

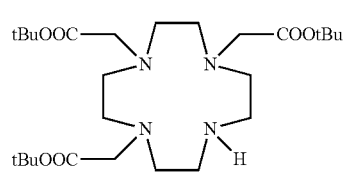

1A in which all carboxyl groups are suitably protected as tert-butyl esters, may be obtained e.g. as disclosed in *Org. Synth.* 2008, 85, 10.

Appropriate bridging molecules 2 for the use of the invention are commercially available, or may easily be prepared according to procedures known to those skilled in the relevant art. Suitable examples may for instance comprises an amine of formula —$NH_2R_2$ or diamine of formula —$NH(R_2)$—$(CH_2)_r$—$NH(R'_2)$— (in which r, $R_2$, $R'_2$ are as defined for compounds of formula (I)), or suitable functional derivative thereof that are commercially available or may be easily be obtained according to synthetic procedure known to those skilled in the relevant art.

Examples of specific procedures for the preparation of protected bridging molecules 2, their coupling with the appropriate substrate molecule 1, and optional conversion of the obtained intermediates to the desired compound of formula (I) are provided in the experimental section, together with relevant operational details.

As a general reference on possible protecting groups, and cleavage conditions, e.g. to implement the step e) of the above general synthetic procedure, see the above cited "T. W. Green and P. G. M. Wuts; Protective groups in organic synthesis" Wiley 3$^{rd}$ Ed. Chapters 5 and 7.

The complexation of the compounds of formula (I) e.g. obtained from step f) of former general preparation scheme with a paramagnetic ion and, particularly, with gadolinium, may be performed, for instance, by stoichiometric addition of a suitable Gd(III) derivative, particularly a Gd(III) salt or oxide, to a solution of the ligand, e.g. by working according to well-known experimental methods, for instance as reported in EP 230893.

Finally, optional salification of the compounds of the invention may be carried out by properly converting any of the free acidic groups (e.g. carboxylic, phosphonic or phosphinic) or free amino groups into the corresponding pharmaceutically acceptable salts. In this case too, the operative conditions being employed for the optional salification of the compounds of the invention are all within the ordinary knowledge of the skilled person.

Exemplificative implementation of the above general procedure leading to the compounds of the formula (I) and of the chelate complexes thereof, are schematized herein below.

For instance, dimeric compounds according to the invention may conveniently be prepared by using the synthetic procedure schematized in the following general Scheme 1

Scheme 1
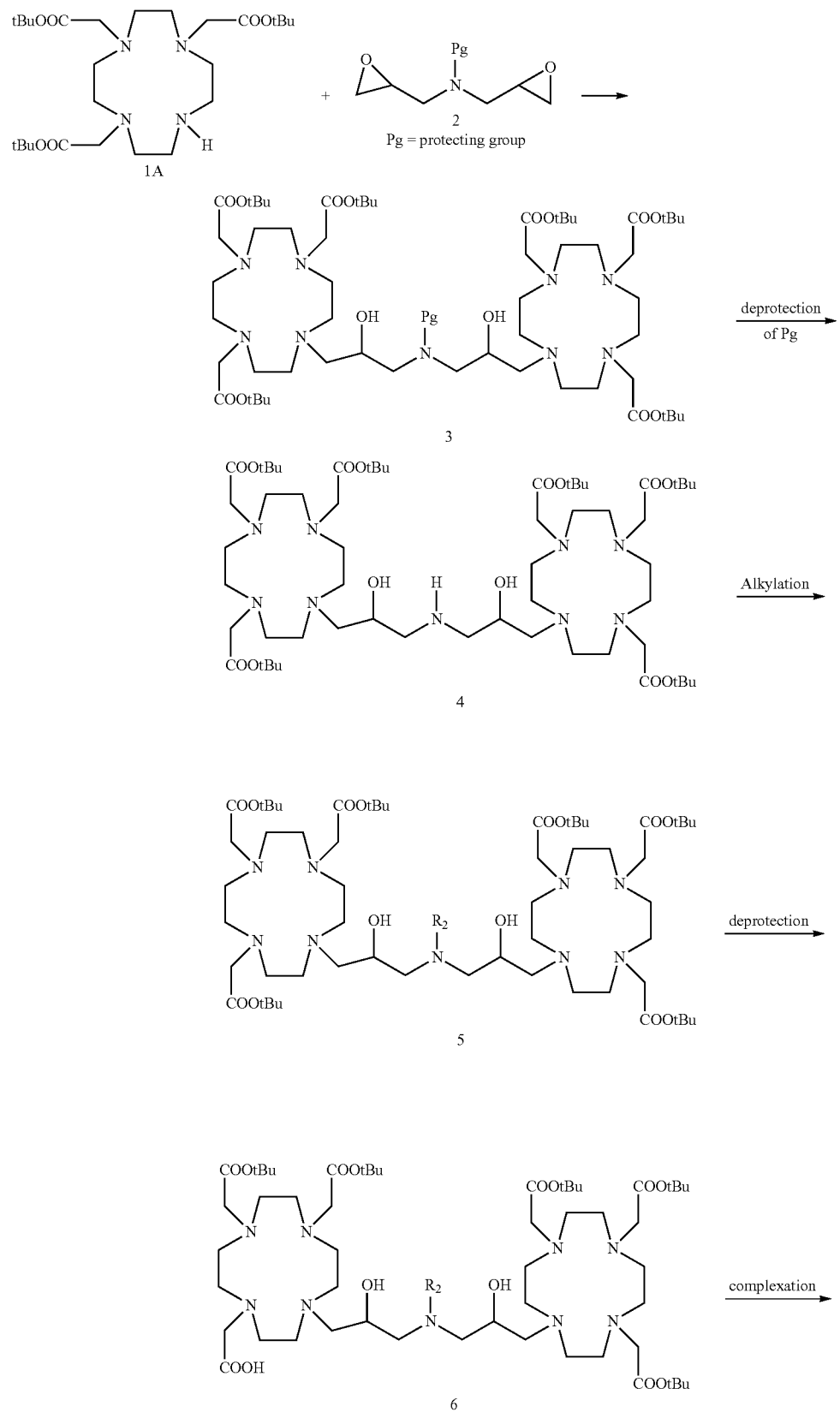

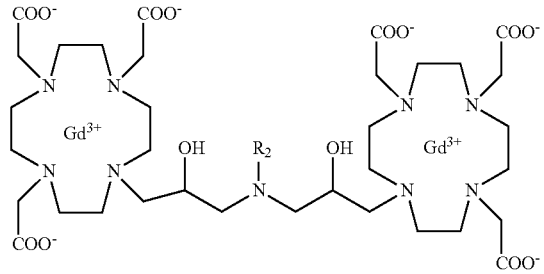

in which the bis-epoxide 2 is reacted with two units of substrate 1A to give an intermediate 3 in which the nitrogen atom (of the bridging moiety) is in a protected form which is first deprotected and then alkylated with the appropriate $R_2$ group to give the protected dimer of formula (II) that after cleavage of carboxy-protecting groups is complexed with the gadolinium metal ion to give the desired bis-Gd complex of formula (I).

Compounds of formula (IV) comprising a bridging molecule interrupted by two nitrogen atom may be analogously obtained, by using a corresponding bis-epoxide 2 comprising two suitably protected or alkylated nitrogen atoms.

Dimeric compounds of formula (I) may alternatively be prepared by using the synthetic procedure schematized in the following Scheme 2

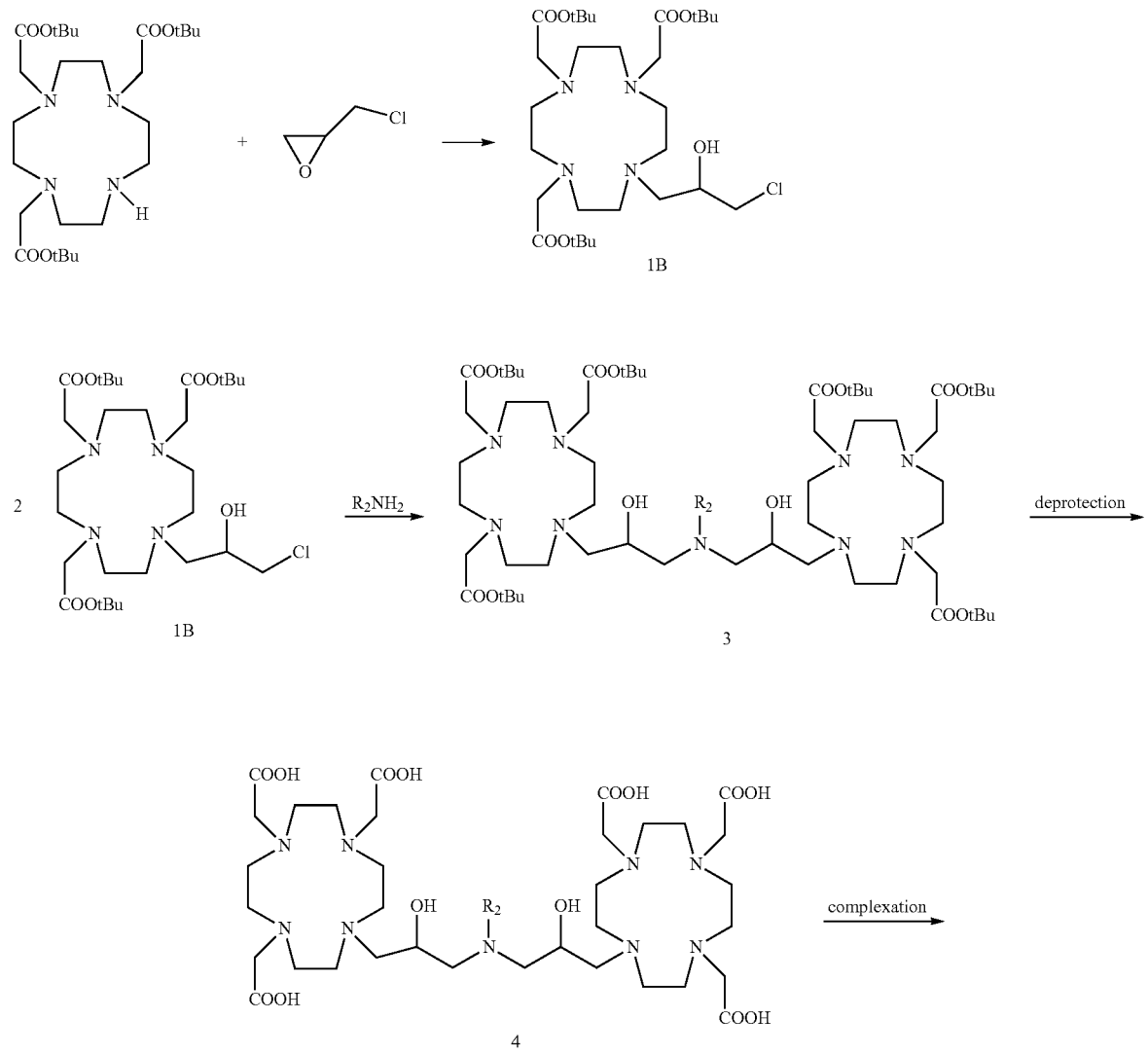

-continued

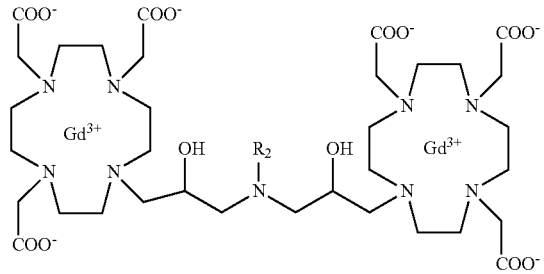

5

According to this approach, a suitably protected Substrate 1B

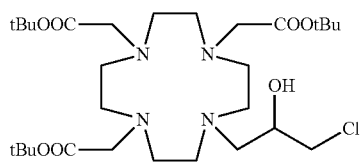

1B is first obtained, e.g. by reaction of the commercially available epichlorydrin with the substrate 1A, as described in details in the experimental section, which is then reacted with the appropriated amine $R_2NH_2$ leading to the protected compound of formula 3 that is then deprotected and complexed as above said.

Compounds of formula (IV) comprising a bridging molecule interrupted by two substituted nitrogen atoms may be analogously obtained by using the appropriate bis-amine e.g. of formula $NH(R_2)(CH_2)_rNH(R_2)$.

Specific examples of preparation of preferred compounds of formula (I) according to the invention are moreover provided in the following experimental section, constituting a general reference to the operative conditions being employed in the above processes.

Dimers of formula (I) according to the present invention include two tetraaza macrocycles each having a hydroxylated residue on a nitrogen atom of the macrocyclic cage linked to one another by means of a bridging moiety comprising one or more amine —$NR_2$— group(s).

Dimeric paramagnetic complexes according to the invention, having these peculiar structural components have interestingly proved to display a high relaxivity.

Relaxivity $r_{1p}$ values measured for some representative complex compounds of formula (I) are provided in Table A of the experimental section, by comparison with $r_{1p}$ values measured, at the same conditions, for some known MRI contrast agents currently used in the diagnostic daily practice, e.g. including Gd-DOTA, marketed as DOTAREM®, and Gd-HPDO3A marketed as ProHance®. By definition, relaxivity data, hence including those of the table A, are expressed in terms of gadolinium concentration (mM).

Interestingly, relaxivity $r_{1p}$ values measured for the dimeric complex compounds of the invention are at least to 2 times higher than that recorded for commercial contrast agent of the marker (at the same gadolinium concentration).

In particular, the paramagnetic complex compounds of the formula (I) of the invention display a relaxivity $r_{1p}$ value measured in human plasma, at 37° C. and approx. 1.4 T which is of at least about 6, preferably higher than 7, and more preferably, higher than 8 $mM^{-1} s^{-1}$.

Moreover, the paramagnetic complex compounds of the invention have proven to display a low if not negligible protein binding with human plasma proteins, including, for instance, the HSA.

In addition, the Applicant has observed that the presence of a hydroxylated pendant arm on each macrocyclic cage constituting the dimeric compounds of the invention, beside leading to complex compounds having favorable relaxivity and solubility, may also contribute to obtain aqueous solutions of corresponding complex paramagnetic endowed with optimized viscosity. Advantageously, the high relaxivity displayed by the agents of the invention may allow to reduce their diagnostically effective dose, as compared to current contrast agents. Paramagnetic complexes and, especially, gadolinium complexes of the compounds of formula (I), or the pharmaceutical acceptable salt thereof, thus find advantageous use in the preparation of pharmaceutical formulations intended for a general use in the diagnostic imaging of a human or animal body organ, tissue or region either in vivo or in vitro, ex vivo.

According to a further aspect, the invention relates to the use of the compounds of formula (I) in the form complexes with a paramagnetic metal ion and, especially, gadolinium, or of a pharmaceutical acceptable salt thereof, for the preparation of a pharmaceutical formulation for use in the diagnostic imaging, either in vivo or in vitro, ex vivo, of a human or animal body organ, tissue or region or of a biological sample, including cells, biological fluids and biological tissues originating from a live mammal patient, and preferably, human patient, by use of the MRI technique.

A further aspect of the invention concerns a pharmaceutical composition for diagnostic use comprising a compound of formula (I) in the form of paramagnetic metal complex or of a pharmaceutical salt thereof, in admixture with one or more physiologically acceptable excipients, diluents or solvents. Preferably, the pharmaceutical composition is a contrast-producing composition and, more preferably, a MRI contrast producing composition comprising at least one Gd-complex according to the invention.

In an additional aspect the invention relates to a MRI contrast medium comprising an effective amount of at least one chelated compound according to the invention and, especially, of a gadolinium complex of the formula (I), or of a pharmaceutical acceptable salt thereof, in combination with one or more pharmaceutically acceptable excipients, diluents or solvents.

To this extent, and unless otherwise provided, the term "effective amount" or "effective dose", as used herein, refers to any amount of a paramagnetic chelated complex of the formula (I) according to the invention or pharmaceutical composition thereof, that is sufficient to fulfil its intended diagnostic purpose(s): i.e., for example, to ex vivo visualize a biological element including cells, biological fluids and biological tissues or the in vivo diagnostic imaging of body organs, tissues or regions of a patient.

Unless otherwise indicated, with "individual patient" or "patient" as used herein we refer to a living human or animal patient, and, preferably a human being undergoing MR diagnostic assessment.

Details concerning dosages, dosage forms, modes of administration, pharmaceutically acceptable carriers, excipients, diluents, adjuvants and the like are known in the art.

Interestingly, and as above discussed, suitable dosage of the paramagnetic complexes according to the invention, i.e. allowing to obtain a diagnostically effective visualization of the body organ, tissue or region at least comparable to that obtained in the daily practice with the MRI contrast agents of the market, may include an amount of the paramagnetic complex lower than that currently used with Non-Specific contrast agents of the market.

For instance, satisfactory diagnostic MRI images, providing a physician with adequate diagnostic support, may be obtained with doses of the gadolinium complex compounds identified by the present invention of about 90%, more preferably 80%, and up to 60% of the dose of MRI contrast agent used in the daily practice, which for adult patients commonly is of about 0.1 mmol/kg of patient body weight.

From all the foregoing it can be easily envisaged that the selection of paramagnetic complex compounds of formula (I) identified by the present invention have a wide range of applications as they can be used for intravasal, (for instance intravenous, intraarterial, intracoronaric, intraventricular administration and the like), intrathecal, intraperitoneal, intralymphatic and intracavital administrations. Furthermore, they are suitable for the oral or parenteral administration and, therefore, specifically for the imaging of the gastrointestinal tract.

For instance, for parenteral administration they can be preferably formulated as sterile aqueous solutions or suspensions, whose pH can range from 6.0 to 8.5.

These formulations can be lyophilized and supplied as they are, to be reconstituted before use.

For the gastrointestinal use or for injection in the body cavities, these agents can be formulated as a solution or suspension optionally containing suitable excipients in order, for example, to control viscosity.

For the oral administration they can be formulated according to preparation methods routinely used in the pharmaceutical technique or as coated formulations to gain additional protection against the stomach acidic pH thus preventing, in case of chelated metal ions, their release which may take place particularly at the typical pH values of gastric fluids.

Other excipients, for example including sweeteners and/or flavouring agents, can also be added, according to known techniques of pharmaceutical formulations.

The solutions or suspensions of the compounds of this invention can also be formulated as aerosol to be used in aerosol-bronchography and instillation.

For example, they can be also encapsulated into liposomes or even constitute the liposomes themselves, as set forth above, and thus can be used as uni- or multi-lamellar vesicles.

In a preferred aspect, pharmaceutical compositions according to the invention are properly formulated in isotonic sterile aqueous, optionally buffered, solutions for parenteral administration, and most preferably for intravenous or intra-arterial administration.

More preferably, the said diagnostic composition has a concentration of the paramagnetic complex of the formula (I) of from 0.002 and 1.0 M and is supplied, for instance as a bolus, or as two or more doses separated in time, or as a constant or non-linear flow infusion.

In a further aspect, the invention relates to the use of a pharmaceutical composition including a paramagnetic chelated complex of the formula (I) or pharmaceutical acceptable salt thereof for the diagnostic imaging, both in vitro (ex vivo) and in vivo, of pathological systems, including cells, biological fluids and biological tissues originating from a live mammal patient, and preferably, human patient, as well as of human body organ, regions or tissues, including tumors or cancerous tissues, inflammations, as well as for monitoring the progress and results of therapeutic treatment of the said pathologies.

In an additional aspect, the present invention concerns a method for the in vivo imaging of a body organ, tissue or region by use of the MRI technique, said method comprises enhancing the signal generated by the water protons by use of a paramagnetic chelated complex of the formula (I) according to the invention, or a physiological acceptable salt thereof.

In one embodiment, said method comprises administering to a human or animal patient to be imaged a diagnostically effective amount of a composition of the invention comprising a compound of formula (I) in the form of complex with a paramagnetic metal ion, and, preferably, with the $Gd^3$ metal ion and then subjecting the administered patient to the diagnostic imaging by use of the MRI technique.

According to a particularly preferred embodiment, the above MRI method is instead performed on human or animal bodies suitably pre-administered with a diagnostically effective amount of a composition of the invention as above defined.

More particularly, according to a preferred embodiment the present invention refers to a method for the in vivo imaging a human or animal body organ or tissue by use of the MRI technique that comprises the steps of:

a) submitting a human or animal pre-administered with a composition of the invention comprising a compound of formula (I) in the form of a paramagnetic complex, or of a pharmaceutically acceptable salt thereof, and positioned in a MRI imaging system, to a radiation frequency selected to excite the non-zero proton spin nuclei of the active paramagnetic substrate; and b) recording a MR signal from said excited nuclei.

In yet another aspect the invention provides a method for the in vitro (ex vivo) imaging of biological samples, including cells, biological fluids and biological tissues originating from a live mammal patient, and preferably, human patient, by use of the MRI technique, that comprises contacting an effective amount of a paramagnetic complex compound of formula (I), or of a physiologically acceptable salt thereof, with the biological sample of interest and then obtaining MRI signals from said samples by use of the MRI technique.

Non-limiting examples of preferred compounds of the invention and intermediates for their preparation is reported in the following section, aimed to illustrate the invention in greater detail without limiting its scope.

EXPERIMENTAL PART

Example 1: Preparation of the Substrate 1B

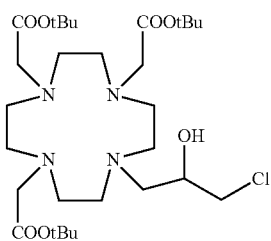

This compound was obtained by using the synthetic procedure shown in Scheme 3:

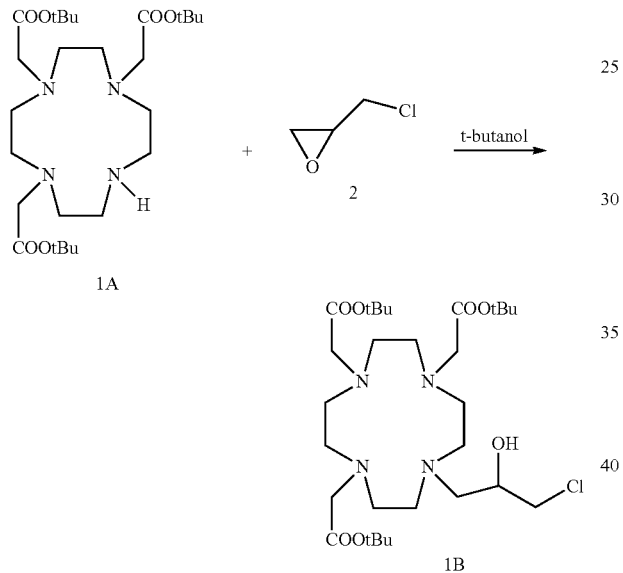

comprising:

a) Preparation of Compound 1B.

Commercially available epichlorohydrin 2 (10.5 mL; 137 mmol) was dissolved in acetonitrile (300 mL) and the resulting solution was slowly added at room temperature to a solution of DO3A tris-t-butyl ester 1A (*Org. Synth.* 2008, 85, 10) (14.1 g; 27.4 mmol) in acetonitrile (100 mL). The mixture was stirred for 24 h then more epichloridrin 2 (5.2 mL; 68 mmol) was added. After 24 h the mixture was evaporated and the residue purified by chromatography on silica gel (eluent: CH$_2$Cl$_2$/MeOH=50:1→1:1) to give compound IC (10.6 g). Yield 64%.

1H-NMR, 13C-NMR and mass spectrum were consistent with the expected structure.

Example 2: Preparation of the Chelate Complex 1

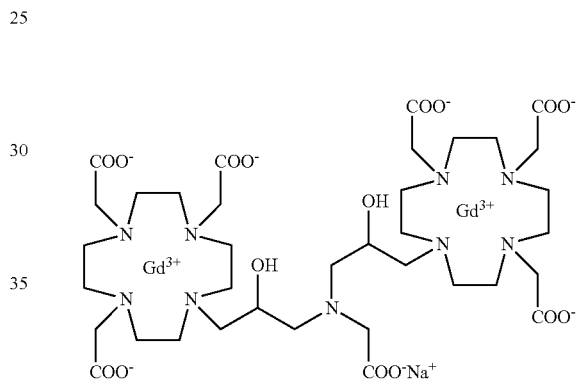

This dimeric compound was prepared using the procedure of the following general Scheme 4:

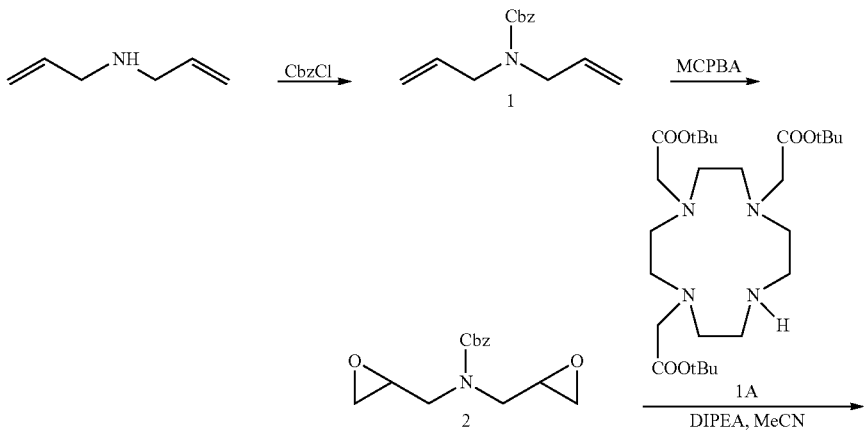

-continued
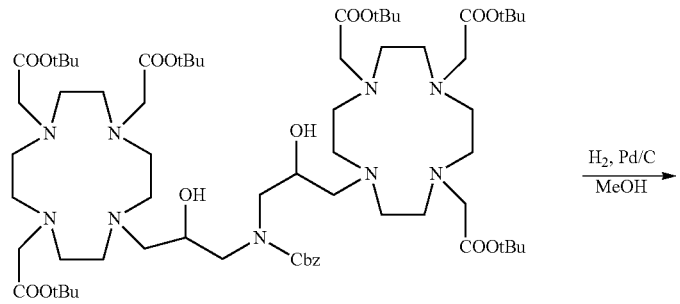
3
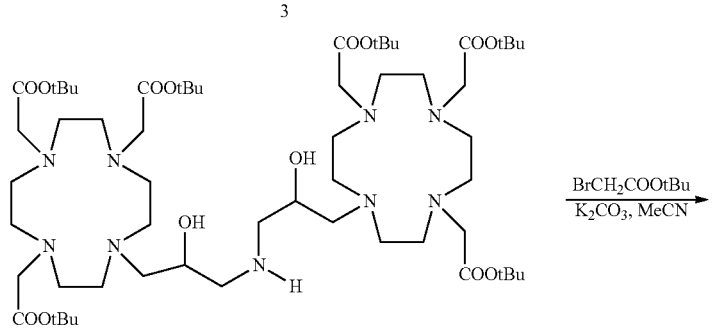
4
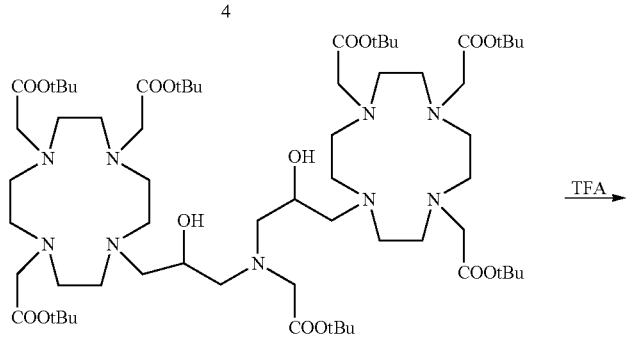
5
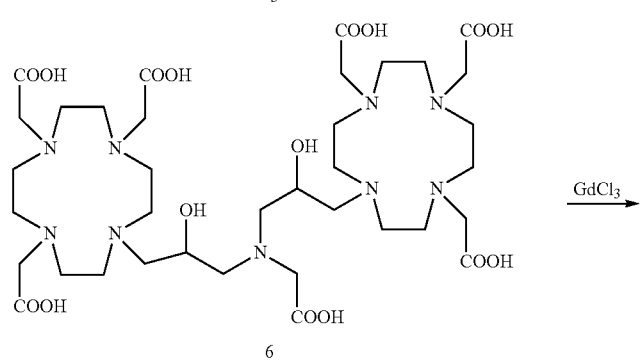
6
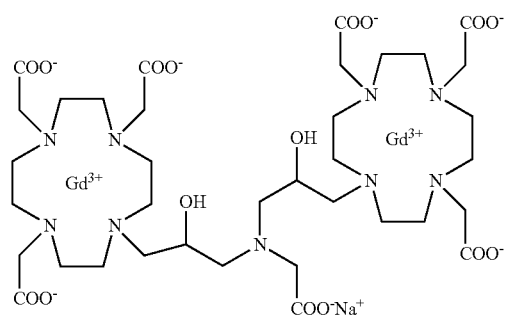

including:

a) Preparation of 1

Benzyl chloroformate (95%; 18.85 g; 105 mmol) was added in 1 h to a mixture of 10 diallylamine (commercially available) (9.7 g; 100 mmol), $K_2CO_3$ (34.5 g; 250 mmol), water (150 mL) and EtOAc (150 mL) at 0° C. After stirring for 6 h, the organic phase was separated and extracted with 1 N HCl (2×100 mL), water (100 mL) and brine (100 mL). The organic phase was dried ($Na_2SO_4$) and evaporated to give 1 (22 g). Yield 95%.

1H-NMR, 13C-NMR and mass spectrum were consistent with the expected structure.

b) Preparation of Protected Bridging Molecule 2

A solution of 3-chloroperbenzoic acid (MCPBA) (75%; 34.5 g; 150 mmol) in dichloromethane (100 mL) was added dropwise to a solution of intermediate 1 (11.6 g; 50 mmol) in dichloromethane (100 mL). The solution was stirred at room temperature for 16 h. More MCPBA (11.5 g) was added and the mixture stirred for other 48 h. The mixture was filtered, washed with 10% aq. $Na_2SO_3$ (2×100 mL), 5% aq. $NaHCO_3$ (4×100 mL), $H_2O$ (100 mL) and brine (100 mL). The organic phase was separated, evaporated and the residue purified by chromatography on silica gel (eluent: n-heptane/EtOAc=2:1) to obtain 2 (11.7 g). Yield 89%.

1H-NMR, 13C-NMR and mass spectrum were consistent with the expected structure.

c) Preparation of Intermediate 3

A solution of Substrate 1A (Org. Synth. 2008, 85, 10) (43.2 g; 84 mmol), intermediate 2 (10 g; 38 mmol) and N,N-diisopropylethylamine (DIPEA) (216 g; 1.68 mol) in acetonitrile (500 mL) was stirred at 60° C. for 48 h. The mixture was evaporated to a residue which was dissolved in EtOAc (300 mL). The solution was washed with water (4×100 mL), brine (4×100 mL), filtered and evaporated to a residue that was purified by flash chromatography on silica gel (eluent: EtOAc/MeOH=1:1) to give intermediate 3 (30 g). Yield 61%.

1H-NMR, 13C-NMR and mass spectrum were consistent with the expected structure.

d) Preparation of Intermediate 4

Palladium 5% carbon (wet with about 50% water) (5 g) was added to a solution of intermediate 4 (25 g; 19.3 mmol) in MeOH (300 mL). The mixture was stirred and hydrogenated at room temperature and atmospheric pressure for 8 h. The mixture was filtered and evaporated to give intermediate 4 (21.5 g). Yield 96%.

1H-NMR, 13C-NMR and mass spectrum were consistent with the expected structure.

e) Preparation of Protected Ligand 5

A solution of t-butyl bromoacetate (3.7 g; 19 mmol) in acetonitrile (50 mL) was added in 30 min to a mixture of compound 5 (20 g; 17.3 mmol) and $K_2CO_3$ (5.53 g; 40 mmol) in acetonitrile (200 mL). The mixture was stirred for 48 h at room temperature then filtered and evaporated. The residue was purified by chromatography on silica gel (eluent: gradient of EtOAc/MeOH) to give 5 (19.4 g). Yield 88%.

1H-NMR, 13C-NMR and mass spectrum were consistent with the expected structure.

f) Preparation of Ligand 6

Trifluoroacetic acid (19 mL) was added to a solution of intermediate 6 (15.3 g; 12 mmol) in dichloromethane (70 mL) at 0° C. The mixture was stirred for 6 h then evaporated; the residue was dissolved in TFA (80 mL) and triisopropylsilane (0.5 mL) was added. The mixture was stirred at room temperature for 16 h, then evaporated. The solid was purified by chromatography on Amberchrome CG161M column (eluent: gradient of water/MeCN) obtaining the chelating ligand 6 as a solid (8.76 g). Yield 83%.

1H-NMR, 13C-NMR and mass spectrum were consistent with the expected structure.

g) Complexation

Gadolinium chloride hexahydrate (3.38 g, 9.1 mmol) was added to a solution of chelating ligand 7 (8 g; 9.1 mmol) in water (100 mL) and the pH of the mixture was slowly increased to pH 6.5-7 with 1 N NaOH. The obtained solution was stirred at room temperature for 5 h then filtered on Millipore HA 0.45 μm, concentrated and purified by chromatography on Amberchrome CG161M column (eluent: gradient of water/MeCN) obtaining 10.1 g of the corresponding gadolinium complex. Yield 92%.

Mass spectrum and elemental analysis were consistent with the expected structure.

Applying the same synthetic strategy and employing the triflate of hydroxymethylphosphonate di-t-butyl ester (synthesized as reported in US2014/0086846, page 33) the Chelate Complex 2 was prepared.

Example 3: Preparation of the Chelate Complex 3

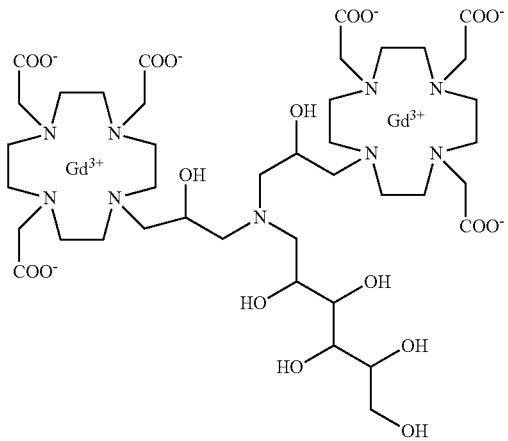

This complex compound was obtained by using the procedure shown in Scheme 5:

Scheme 5
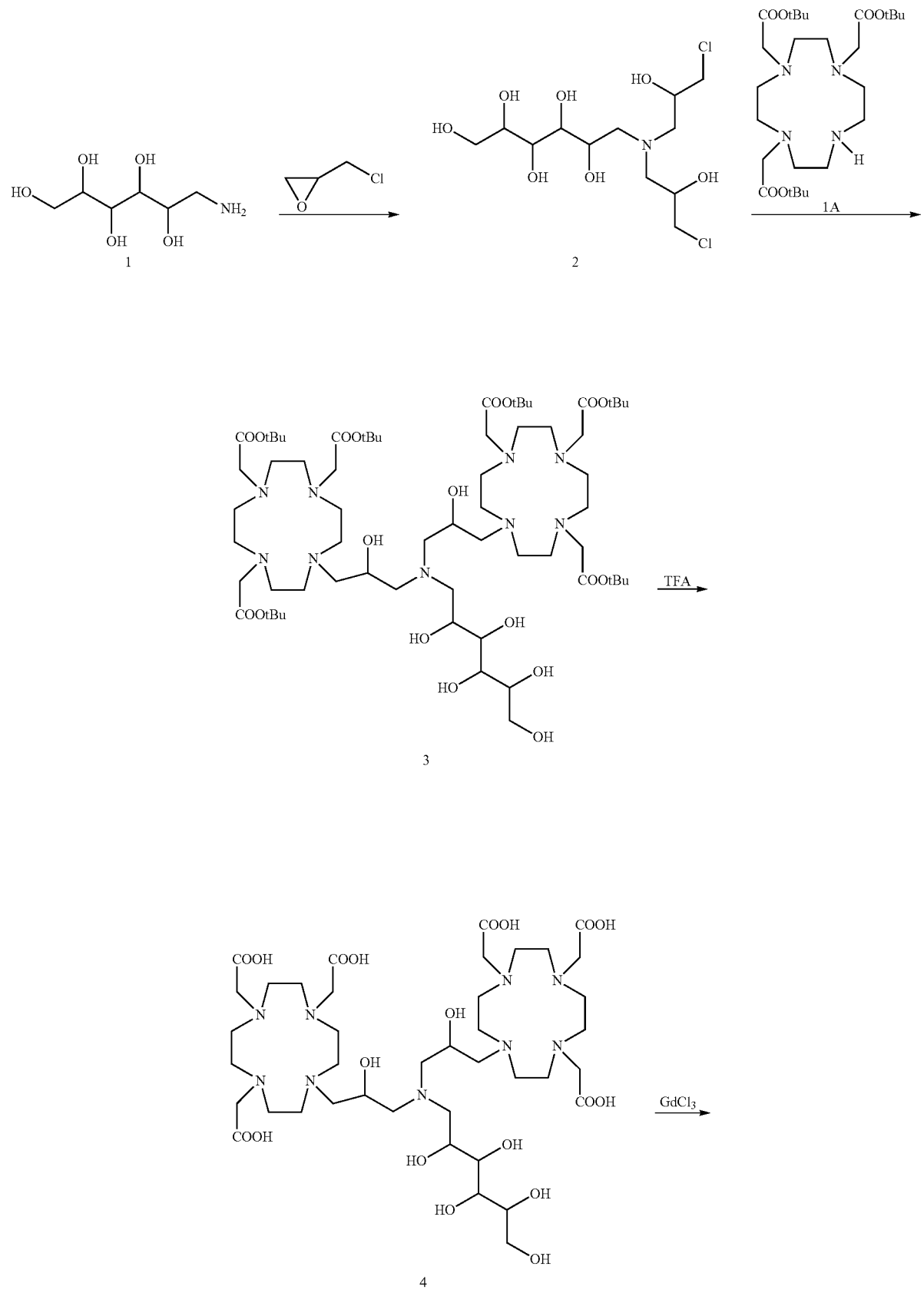

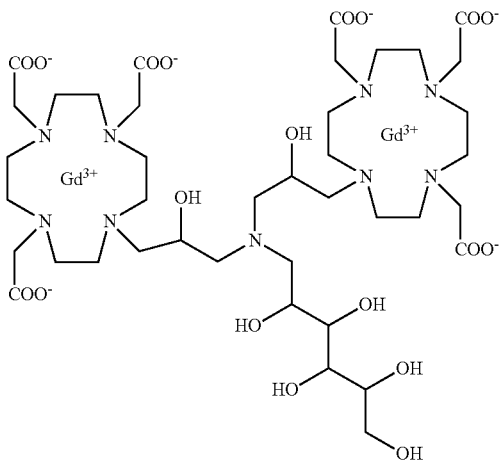

Including:

a) Preparation of 2

Commercially available epichlorohydrin (4.1 mL; 52 mmol) was added to a solution of commercially available D-glucamine 1 (1.9 g; 10.5 mmol) in MeOH (110 mL). The mixture was stirred at 50° C. for 26 h then evaporated to give the bridging molecule 2 as a colourless oil that was directly used for the next reaction without any further purification. Quantitative yield.

1H-NMR, 13C-NMR and mass spectrum were consistent with the expected structure.

b) Preparation of 3

A solution of Substrate 1A (Org. Synth. 2008, 85, 10) (10.7 g; 21 mmol) in acetonitrile (14 mL) was added to a solution of compound 2 (3.8 g; 10.5 mmol) in DMSO (14 mL) and Et$_3$N (4.3 mL). The mixture was stirred at 70° C. for 72 h then evaporated. The residue was purified by chromatography on Amberlite XAD 1600 (eluent: gradient of water/MeCN) to give the protected ligand 3 (2.1 g). Yield 15%.

1H-NMR, 13C-NMR and mass spectrum were consistent with the expected structure.

c) Preparation of Ligand 4

Trifluoroacetic acid (1.1 mL) was added to a solution of 3 (2.1 g; 1.6 mmol) in dichloromethane (30 mL). The mixture stirred for 30 min then was evaporated. The residue was dissolved in TFA (3.7 mL) and triisopropylsilane (0.1 mL) was added. The obtained mixture was stirred for 24 h at room temperature then evaporated and the residue purified by chromatography on Amberlite XE 750 column (eluent: gradient of water/MeCN) obtaining the desired ligand 4 (1.5 g). Yield 95%.

1H-NMR, 13C-NMR and mass spectrum were consistent with the expected structure.

d) Complexation

Ligand 4 (1.5 g; 1.5 mmol) was dissolved in water (20 mL), gadolinium chloride hexahydrate (1.13 g; 3 mmol) was added then 1M NaOH was added to achieve pH 7. The mixture was stirred at 50° C. for 6 h. The solution was then filtered on Millipore HA 0.25 μm filters and evaporated under reduced pressure. The crude product was purified on Amberchrome CG161M column (eluent: gradient of water/acetonitrile). The fractions containing the pure product were pooled and evaporated. The solid product was dried under vacuum to obtain the gadolinium complex as a white powder (1.4 g). Yield 72%.

Mass spectrum and elemental analysis were consistent with the expected structure.

Applying the same synthetic strategy and employing the 2-[2-(aminomethyl)-3-[2-hydroxy-1-(hydroxymethyl)ethoxy]propoxy]-1,3-propanediol (prepared for instance as reported in Chem. Commun. 2005, 474-476) the Chelate Complex 8 was prepared.

Example 4: Preparation of the Chelate Complex 5

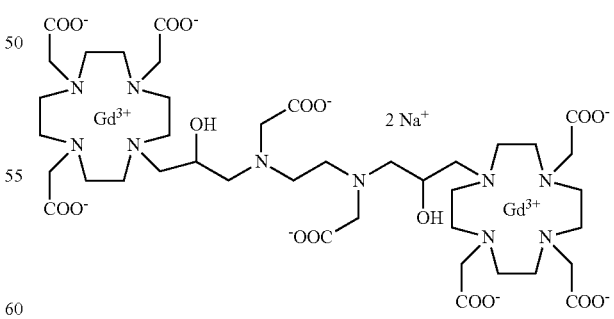

This complex compound was obtained by using the procedure shown in Scheme 6:

Scheme 6
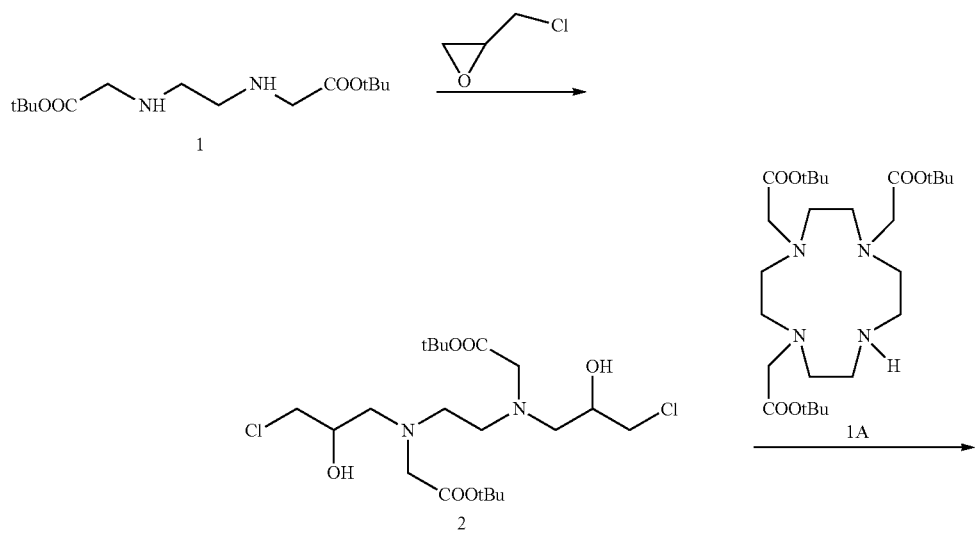
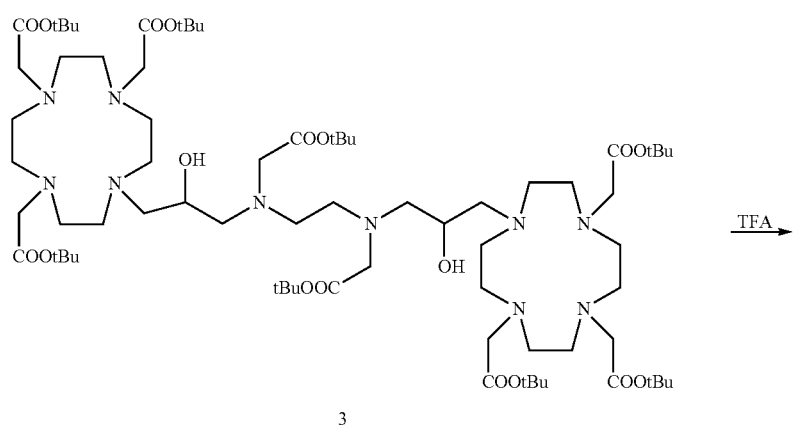
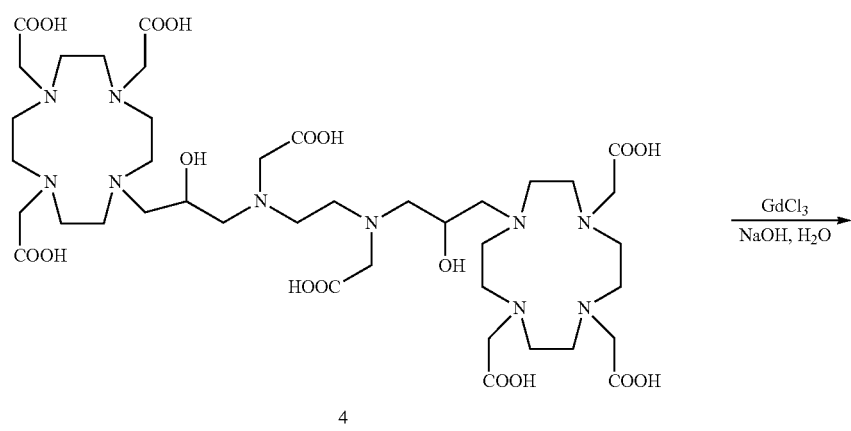

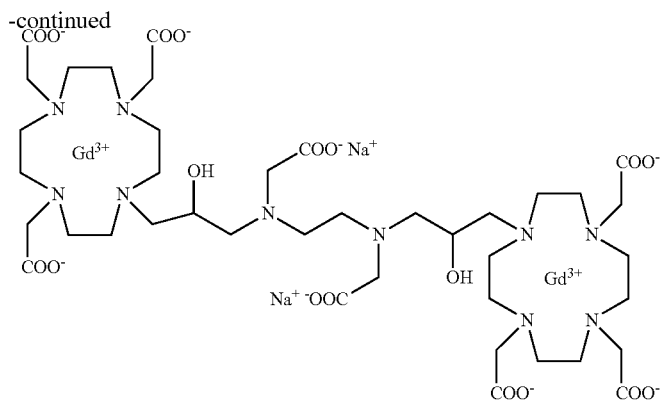

including:

a) Preparation of 2

Epichlorohydrin (3.7 g; 40 mmol) was added to a solution of 1 (prepared as reported in Tetrahedron 2010, 66, 8594-8604) (2 g; 7 mmol) in MeOH (40 mL). The reaction mixture was stirred at room temperature for 56 h. The white solid precipitated was filtered and dried to give compound 2 (3.28 g). Yield 55%.

1H-NMR, 13C-NMR and mass spectrum were consistent with the expected structure.

b) Preparation of Protected Ligand 3

Substrate 1A (Org. Synth. 2008, 85, 10) (15 g; 29 mmol) was added to a solution of compound 2 (4.2; 8.9 mmol) and $Et_3N$ (3.6 g; 36 mmol) in MeCN (60 mL). The mixture was stirred at 50° C. for 48 h then at 70° C. for 20 h. The mixture was evaporated, the residue treated with EtOAc (100 mL) and filtered. The organic phase was washed with water (2×100 mL), brine (2×100 mL) then evaporated. The residue was purified by flash chromatography on silica gel (eluent: $CH_2Cl_2$/MeOH=100:1→1:1) to give the protected ligand 3 as pale yellow oil (4.55 g). Yield 36%.

1H-NMR, 13C-NMR and mass spectrum were consistent with the expected structure.

c) Preparation of Ligand 4

Trifluoroacetic acid (6 mL; 48 mmol) and triisopropylsilane (0.1 mL) were added to compound 3 (4.5 g, 3 mmol). The solution was stirred at room temperature for 24 h. The solvent was evaporated and the residue purified by chromatography on Amberlite XE 750 column (eluent: gradient of water/MeCN) obtaining the desired ligand 4 (3 g). Yield 96%.

1H-NMR, 13C-NMR and mass spectrum were consistent with the expected structure.

d) Complexation

Ligand 4 (3 g; 3 mmol) was suspended in water (60 mL) and gadolinium chloride hexahydrate (2.27 g; 6.1 mmol) was added. 1M NaOH was added to achieve pH 7 and the homogeneous solution was stirred at 50° C. for 2 h. The solution was then filtered on Millipore HA 0.25 μm filters and evaporated under reduced pressure. The crude product was purified on resin Amberchrome CG161M column (eluent: water/acetonitrile). The fractions containing the pure product were pooled and evaporated. The solid product was dried under vacuum to obtain the gadolinium complex as a white powder (2 g). Yield 49%.

Mass spectrum and elemental analysis were consistent with the expected structure.

Example 5: Preparation of the Chelate Complex 7

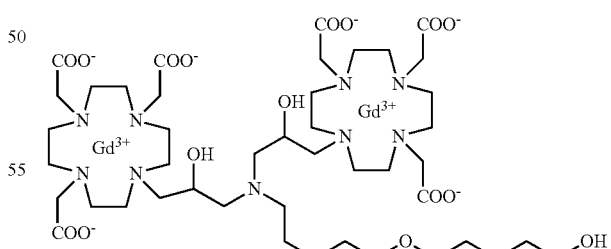

This complex compound was obtained by using the procedure shown in Scheme 7:

Scheme 7
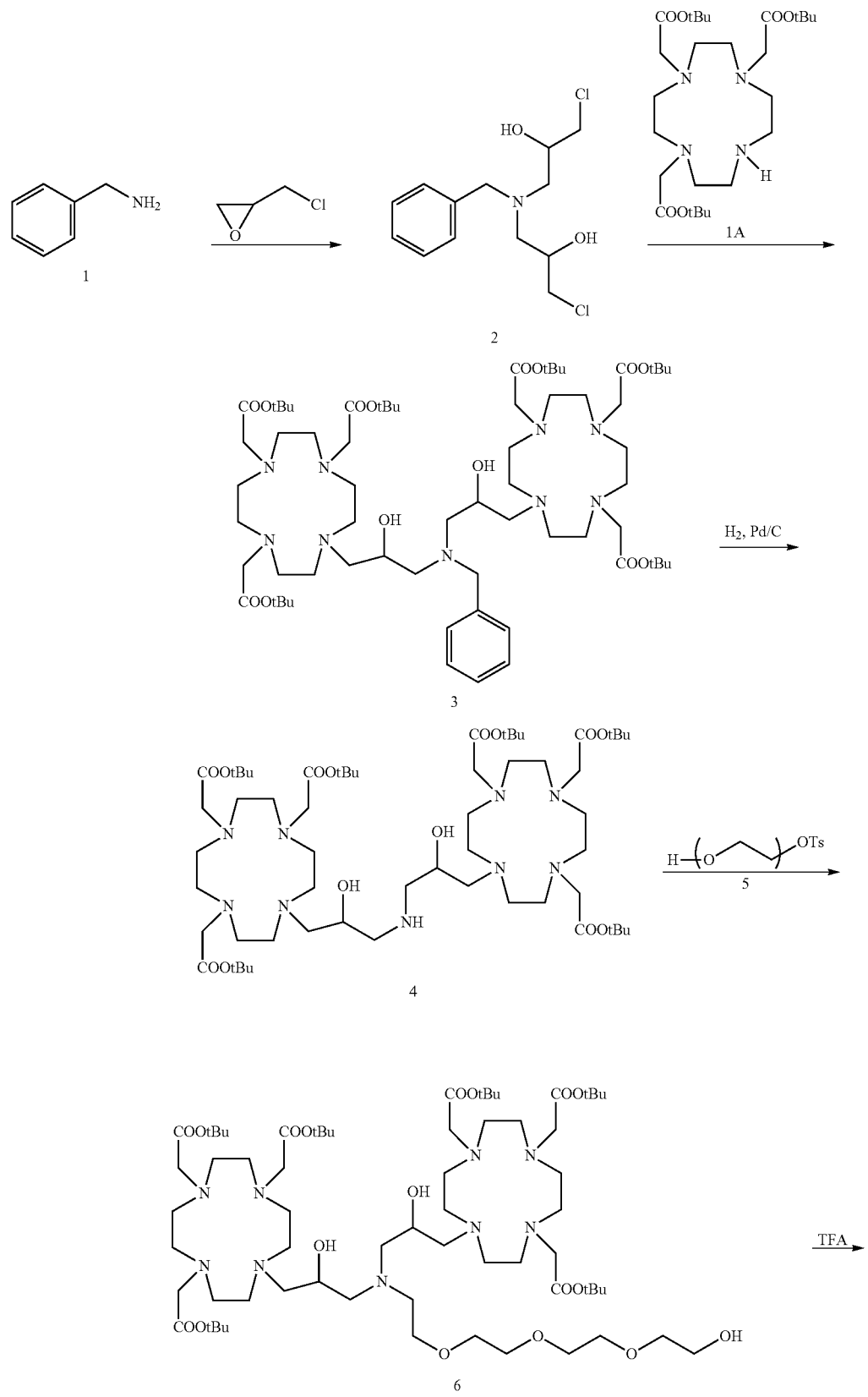

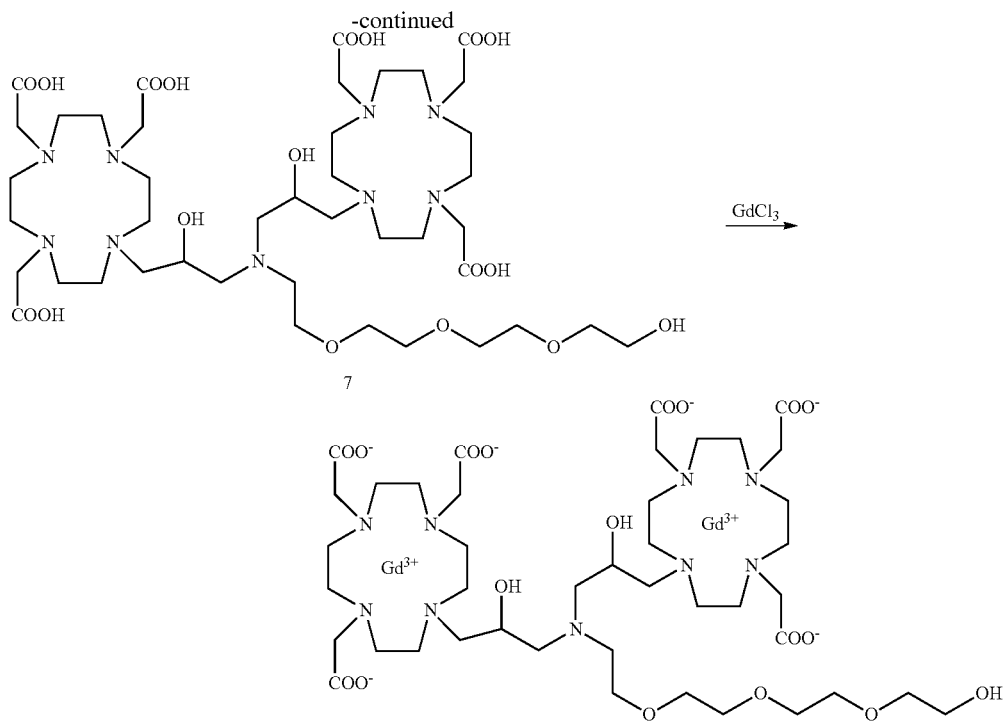
-continued a) Preparation of 2

Epichlorohydrin (2.8 mL; 36 mmol) was added to a solution of commercially available benzylamine 1 (1.64 g; 15 mmol) in EtOH (10 mL). The mixture was stirred at room temperature for 30 h then evaporated to give the protected bridging molecule 2 that was directly used for the next reaction without any further purification. Quantitative yield.

1H-NMR, 13C-NMR and mass spectrum were consistent with the expected structure.

b) Preparation of Intermediate 3

A solution of substrate 1A (Org. Synth. 2008, 85, 10) (15.4 g; 30 mmol) in MeCN (30 mL) was added to a solution of compound 2 (438 g; 15 mmol) in MeCN (30 mL) and Et$_3$N (6.3 mL). The mixture was stirred at 55° C. for 96 h then evaporated. The residue was purified by flash chromatography on silica gel (eluent: CH$_2$Cl$_2$/MeOH=100:1→1:1) to give intermediate 3 (10 g). Yield 53%.

1H-NMR, 13C-NMR and mass spectrum were consistent with the expected structure.

b) Preparation of 4

A solution of intermediate 3 (10 g; 8 mmol) in methanol (80 mL) was added with 5% palladium on carbon (wet with about 50% water) (2.5 g) and hydrogenated at 45° C. for 5 h. More catalyst (0.8 g) was added and the mixture hydrogenated at 45° C. for other 4 h The catalyst was filtered and the solution evaporated to give intermediate 4 (8.9 g). Yield 96%.

1H-NMR, 13C-NMR and mass spectrum were consistent with the expected structure.

c) Preparation of the Protected Ligand 6

Tetraethylene glycol monotosylate 5 (2.6 g, 7.5 mmol) (commercial product, e.g. Aldrich) was added to a solution of 4 (8.5 g; 7.3 mmol) in MeCN (mL) and the mixture was stirred for 72 h. The mixture was evaporated, the residue dissolved in CHCl$_3$ (200 mL) and washed with water (2×100 mL). The organic phase was separated, dried and evaporated. The residue was purified by flash chromatography on silica gel (eluent: CH$_2$Cl$_2$/MeOH=100:1→1:1) to give the protected ligand 6 (8.2 g). Yield 88%.

1H-NMR, 13C-NMR and mass spectrum were consistent with the expected structure.

d) Preparation of the Ligand 7

Trifluoroacetic acid (5 mL) was added to a solution of intermediate 6 (8 g; 6.3 mmol) in dichloromethane (50 mL). The mixture stirred for 30 min then was evaporated. The residue was dissolved in TFA (20 mL) and triisopropylsilane (0.1 mL) was added. The obtained mixture was stirred for 24 h at room temperature then evaporated and the residue purified by chromatography on Amberlite XE 750 column (eluent: gradient of water/MeCN) obtaining the desired ligand 7 (5.3 g). Yield 84%.

1H-NMR, 13C-NMR and mass spectrum were consistent with the expected structure.

d) Complexation

Ligand 7 (4.5 g; 4.5 mmol) was dissolved in water (100 mL), gadolinium chloride hexahydrate (1.7 g; 4.6 mmol) was added then 1M NaOH was added to achieve pH 7. The mixture was stirred at 50° C. for 18 h. The solution was then filtered on Millipore HA 0.25 μm filters and evaporated under reduced pressure. The crude product was purified on Amberchrome CG161M column (eluent: gradient of water/acetonitrile). The fractions containing the pure product were pooled and evaporated. The solid product was dried under vacuum to obtain the gadolinium complex as a white powder (4.4 g). Yield 75%.

Mass spectrum and elemental analysis were consistent with the expected structure.

Applying the same synthetic strategy and employing the 2-(2-hydroxyethoxy)ethyl 4-methylbenzenesulfonate (commercially available) the Chelate Complex 4 was prepared.

Example 6: Relaxometric Properties

The relaxometric properties of some representative complex compounds according to the invention have been determined at different magnetic field strengths, e.g. including 0.47 and 1.41 T, at 37° C. and in different media (physiologic solution and human plasma) and compared with relaxivity values measured, at the same conditions, for some Gd-Complex of the market having an analogous cyclic coordination cage.

Materials

Apparatus

The longitudinal water proton relaxation rate ($R_1 = 1/T_1$) was measured at 0.47 T with a Minispec MQ-20 spectrometer (Bruker Biospin, Germany) operating at a proton Larmor frequency of 20 MHz; MR experiments at 1.41 T were performed using a Minispec MQ-60 spectrometer (Bruker Biospin, Germany) operating at a proton Larmor frequency of 60 MHz.

Methods

Sample Preparation

All test articles were used as supplied and diluted in the selected medium (physiologic solution or human plasma) by weighting the required amount of paramagnetic chelated complex to get a 5 or 10 mM starting solution.

Relaxivity Measurements

Five different concentration samples (0.1, 0.25, 0.5, 0.75 and 1 mM) for each medium have been prepared by further dilution of the starting 5 or 10 mM solution.

Relaxation Measurement

Relaxivity measurements were performed at 0.47 T and 1.41 T at a preset temperature sample of 37° C., kept constant by means of a thermostatic bath connected to the sample holder of the spectrometer. The five sample solutions have been preliminary pre-heated at 37° C. in an external thermostatic bath and then left 10 minutes inside the internal bath to assure the stabilization of the temperature. Longitudinal relaxation time $T_1$ was measured by means of a standard inversion recovery sequence, where the inversion time (TI) was varied from 10 ms to at least 5 times $T_1$ in 15 steps. Statistical analysis (mono-exponential fitting for $T_1$ measurement, linear fitting for the evaluation of longitudinal relaxivity) was performed by Mathematica® (Wolfram, USA). Errors on the estimated parameters were evaluated by the fitting procedure.

Results

The relaxivity values $r_{1p}$ obtained from some representative compounds according to the invention, both in physiologic solution and in human plasma, at 37° C., are summarized in the following Table A, together with the structure of tested compounds and the strength of the applied magnetic field (in T), and compared with corresponding values measured for some commercial contrast agents in clinical practice.

By definition, relaxivity data, and hence including those of the table below, are expressed in terms of gadolinium concentration.

TABLE A

| | $r_{1p}$ [mM$^{-1}$s$^{-1}$] | | | |
|---|---|---|---|---|
| Complex | $r_{1p}$ at 0.47 T 37° C., saline | $r_{1p}$ at 0.47 T 37° C., human plasma | $r_{1p}$ at 1.41 T 37° C., saline | $r_{1p}$ at 1.41 T 37° C., human plasma |
| 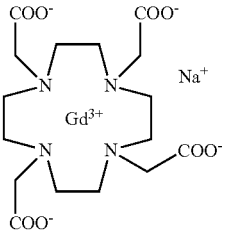 Doratem® | 3.6 | 4.5 | 3.2 | 3.6 |
| 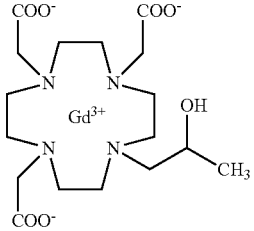 ProHance® | 3.5 | 4.9 | 3.1 | 4.15 |

TABLE A-continued
| | $r_{1p}$ [mM$^{-1}$s$^{-1}$] | | | |
|---|---|---|---|---|
| Complex | $r_{1p}$ at 0.47 T 37° C., saline | $r_{1p}$ at 0.47 T 37° C., human plasma | $r_{1p}$ at 1.41 T 37° C., saline | $r_{1p}$ at 1.41 T 37° C., human plasma |
| 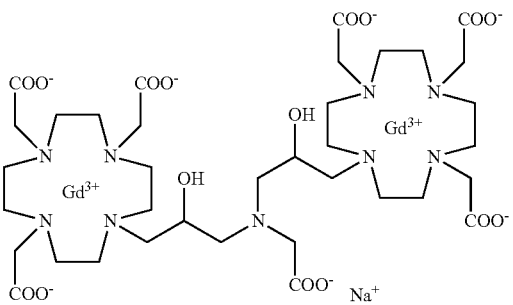  Chelate Complex 1 | 8.3 | 9.7 | 8.5 | 9.2 |
| 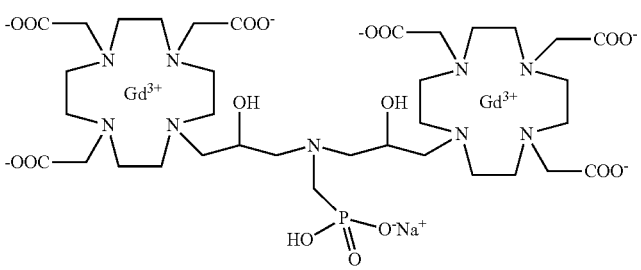  Chelate Complex 2 | 9.0 | 12.0 | 9.3 | 11.3 |
| 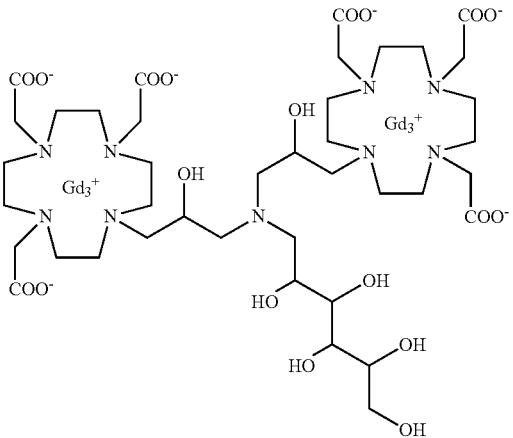  Chelate Complex 3 | 9.3 | 11.5 | 9.4 | 10.8 |
| 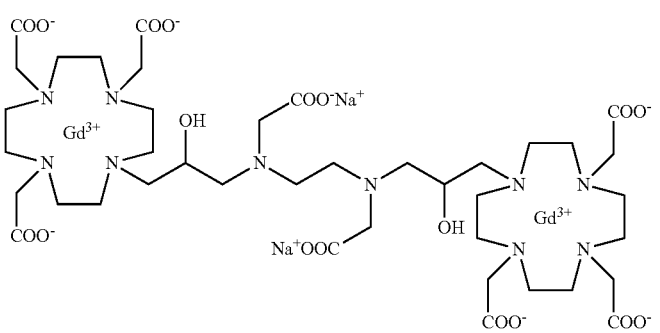  Chelate Complex 5 | 7.3 | 10.6 | 7.5 | 10.2 |

CONCLUSIONS

The relaxivity of the investigated contrast agents ranges between 3.5 (for Prohance®) and 9.0 (for the Chelate Complex 2) mM$^{-1}$ s$^{-1}$ at 0.47 Tin physiologic solution, and from 4.9 to 12.0 mM$^{-1}$ s$^{-1}$ in plasma, same magnetic field, same mMGd$^{3+}$ concentration. These results confirm that the particular selection represented by the paramagnetic complexes and, especially, the Gd$^3$ complexes of the compounds of formula (I) of the invention show an increased relaxivity $r_{1p}$, which is at least about 2 times the relaxivity shown, at the same conditions (i.e. in saline or in human plasma, at 37° C.), by the Non Specific contrast agents currently in use in the daily diagnostic practice, such as Dotarem® and ProHance®.

The invention claimed is:

1. A compound having the following formula (II)

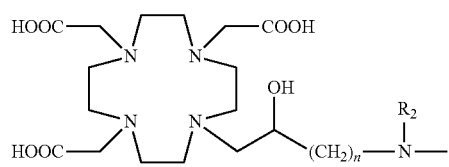
(II)

-continued

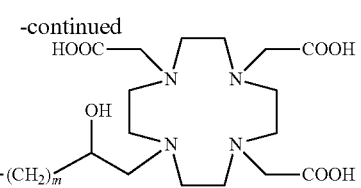

in which:
  m is 1, 2, 3, 4, 5, or 6;
  n is 1 or 2; and
  $R_2$ is a group of formula —(CH$_2$)$_s$CH(R$_3$)-G
  in which
    s is 0, 1 or 2
    $R_3$ is H, or an arylalkylene or cycloalkyl-alkylene having from 1 up to 3 carbon atoms in the alkylene chain;
    G is a group selected from —PO(OR$_4$)$_2$, —PO(R$_5$)(OR$_4$) and —COOH; in which
    $R_4$ independently of one another is H or C$_1$-C$_5$ alkyl;
    $R_5$ is an aryl or a cyclohexyl ring, or C$_1$-C$_5$ alkyl which is optionally substituted by an aryl or cyclohexyl ring
  or a physiologically acceptable salt thereof.

2. The compound according to claim 1 in which $R_3$ is H, having the formula (II B)

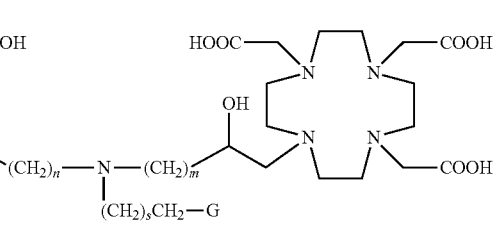
(II B)

in which:
  s is 0, 1 or 2;
  n and m, independently to one another, are 1 or 2; and
  G is a group selected from —PO(OR$_4$)$_2$, —PO(R$_5$)(OR$_4$) and —COOH, in which
    $R_4$ is H or a tert-butyl; and
    $R_5$ is an optionally substituted phenyl or cyclohexyl ring, or a C$_1$-C$_3$ alkyl substituted or not by a phenyl or cyclohexyl ring.

3. The compound according to claim 2 in which in the formula (II B)
  s is 0 or 1;
  n and m are both 1; and,
  G is selected from —PO(OH)$_2$ and —COOH.

4. A chelated complex of a compound according to claim 1 with two paramagnetic metal ions selected from the group consisting of Fe$^{2+}$, Fe$^{3+}$, Cu$^{2+}$, Cr$^{3+}$, Gd$^{3+}$, Eu$^{3+}$, Dy$^{3+}$, La$^{3+}$, Yb$^{3+}$ and Mn$^{2+}$, or a physiologically acceptable salt thereof.

5. The chelated complex according to claim 4, wherein the paramagnetic metal ions are $Gd^{3+}$ ions.

6. The compound according to claim 1, wherein the physiologically acceptable salt is with a cation of (i) an inorganic base selected from an alkali metal and alkaline-earth metal, (ii) an organic base selected from ethanolamine, diethanolamine, morpholine, glucamine, N-methylglucamine, and N,N-dimethylglucamine or (iii) an amino acid selected from lysine, arginine and ornithine.

7. The chelated complex according to claim 4, wherein the physiologically acceptable salt is with a cation of (i) an inorganic base selected from an alkali metal and alkaline-earth metal, (ii) an organic base selected from ethanolamine, diethanolamine, morpholine, glucamine, N-methylglucamine, and N,N-dimethylglucamine or (iii) an amino acid selected from lysine, arginine and ornithine.

8. A pharmaceutical composition comprising a chelated complex of claim 4 and at least one of a pharmaceutically acceptable carrier, a diluent, an excipient and combinations thereof.

* * * * *